(12) United States Patent
Haack et al.

(10) Patent No.: US 9,932,381 B2
(45) Date of Patent: Apr. 3, 2018

(54) EXENDIN-4 DERIVATIVES AS SELECTIVE GLUCAGON RECEPTOR AGONISTS

(71) Applicant: SANOFI, Paris (FR)

(72) Inventors: Torsten Haack, Sulzbach (DE); Siegfried Stengelin, Eppstein-Bremthal (DE); Andreas Evers, Flörsheim (DE); Michael Wagner, Kriftel (DE); Bernd Henkel, Hofheim (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/738,261

(22) Filed: Jun. 12, 2015

(65) Prior Publication Data

US 2015/0368311 A1    Dec. 24, 2015

(30) Foreign Application Priority Data

Jun. 18, 2014  (EP) .................................... 14305935

(51) Int. Cl.
| | | |
|---|---|---|
| *A61K 38/26* | (2006.01) | |
| *A61K 38/00* | (2006.01) | |
| *C07K 14/605* | (2006.01) | |
| *A61K 45/06* | (2006.01) | |
| *C07K 14/575* | (2006.01) | |

(52) U.S. Cl.
CPC ............ *C07K 14/605* (2013.01); *A61K 45/06* (2013.01); *C07K 14/57563* (2013.01); *A61K 38/00* (2013.01)

(58) Field of Classification Search
CPC .............................. A61K 38/26; C07K 14/605
See application file for complete search history.

(56) References Cited

U.S. PATENT DOCUMENTS

| | | | |
|---|---|---|---|
| 5,424,286 | A | 6/1995 | Eng |
| 5,641,757 | A | 6/1997 | Bornstein et al. |
| 6,284,727 | B1 | 9/2001 | Kim et al. |
| 6,329,336 | B1 | 12/2001 | Bridon et al. |
| 6,344,180 | B1 | 2/2002 | Holst et al. |
| 6,410,511 | B2 | 6/2002 | L'Italien et al. |
| 6,429,197 | B1 | 8/2002 | Coolidge et al. |
| 6,451,974 | B1 | 9/2002 | Hansen |
| 6,458,924 | B2 | 10/2002 | Knudsen et al. |
| 6,482,799 | B1 | 11/2002 | Tuse et al. |
| 6,506,724 | B1 | 1/2003 | Hiles et al. |
| 6,514,500 | B1 | 2/2003 | Bridon et al. |
| 6,528,486 | B1 | 3/2003 | Larsen et al. |
| 6,579,851 | B2 | 6/2003 | Goeke et al. |
| 6,593,295 | B2 | 7/2003 | Bridon et al. |
| 6,703,359 | B1 | 3/2004 | Young et al. |
| 6,706,689 | B2 | 3/2004 | Coolidge et al. |
| 6,723,530 | B1 | 4/2004 | Drucker |
| 6,821,949 | B2 | 11/2004 | Bridon et al. |
| 6,828,303 | B2 | 12/2004 | Kim et al. |
| 6,849,714 | B1 | 2/2005 | Bridon et al. |
| 6,858,576 | B1 | 2/2005 | Young et al. |
| 6,861,236 | B2 | 3/2005 | Moll et al. |
| 6,872,700 | B1 | 3/2005 | Young et al. |
| 6,884,579 | B2 | 4/2005 | Holst et al. |
| 6,887,470 | B1 | 5/2005 | Bridon et al. |
| 6,887,849 | B2 | 5/2005 | Bridon et al. |
| 6,894,024 | B2 | 5/2005 | Coolidge et al. |
| 6,902,744 | B1 | 6/2005 | Kolterman et al. |
| 6,924,264 | B1 | 8/2005 | Prickett et al. |
| 6,956,026 | B2 | 10/2005 | Beeley et al. |
| 6,969,702 | B2 | 11/2005 | Bertilsson et al. |
| 6,972,319 | B1 | 12/2005 | Pan et al. |
| 6,982,248 | B2 | 1/2006 | Coolidge et al. |
| 6,989,366 | B2 | 1/2006 | Beeley et al. |
| 6,998,387 | B1 | 2/2006 | Goke et al. |
| 7,056,734 | B1 | 6/2006 | Egan et al. |
| 7,056,887 | B2 | 6/2006 | Coolidge et al. |
| 7,105,489 | B2 | 9/2006 | Hathaway et al. |
| 7,105,490 | B2 | 9/2006 | Beeley et al. |
| 7,115,569 | B2 | 10/2006 | Beeley et al. |
| 7,138,375 | B2 | 11/2006 | Beeley et al. |
| 7,138,546 | B2 | 11/2006 | Tang |
| 7,141,240 | B2 | 11/2006 | Perfetti et al. |
| 7,141,547 | B2 | 11/2006 | Rosen et al. |
| 7,144,863 | B2 | 12/2006 | Defelippis et al. |
| 7,153,825 | B2 | 12/2006 | Young et al. |
| 7,157,555 | B1 | 1/2007 | Beeley et al. |
| 7,179,788 | B2 | 2/2007 | Defelippis et al. |
| 7,189,690 | B2 | 3/2007 | Rosen et al. |
| 7,220,721 | B1 | 5/2007 | Beeley et al. |
| 7,223,725 | B1 | 5/2007 | Beeley et al. |
| 7,256,253 | B2 | 8/2007 | Bridon et al. |
| 7,259,136 | B2 | 8/2007 | Hathaway et al. |
| 7,259,233 | B2 | 8/2007 | Dodd et al. |

(Continued)

FOREIGN PATENT DOCUMENTS

| | | |
|---|---|---|
| CN | 101538323 | 9/2009 |
| CN | 102649947 | 9/2009 |

(Continued)

OTHER PUBLICATIONS

US 8,729,011, 05/2014, Dimarchi et al. (withdrawn)
Bromer, "Chemical Characteristics of Glucagon," Handbook of Experimental Pharmacology 66:1-22 (1983).
Donnelly, "The structure and function of the glucagon-like peptide-1 receptor and its ligands," Br. J. Pharmacol. 166 (1):27-41 (May 2012).
Eng et al., "Isolation and characterization of exendin-4, an exendin-3 analogue, from Heloderma suspectum venom. Further evidence for an exendin receptor on dispersed acini from guinea pig pancreas," J. Biol. Chem. 267(11):7402-5 (Apr. 1992).

(Continued)

*Primary Examiner* — Gyan Chandra

(74) *Attorney, Agent, or Firm* — McDonnell Boehnen Hulbert & Berghoff LLP

(57) ABSTRACT

The present invention relates to glucagon receptor agonists and their medical use, for example in the treatment of severe hypoglycemia.

21 Claims, 5 Drawing Sheets

(56) References Cited

U.S. PATENT DOCUMENTS

Figure 1:
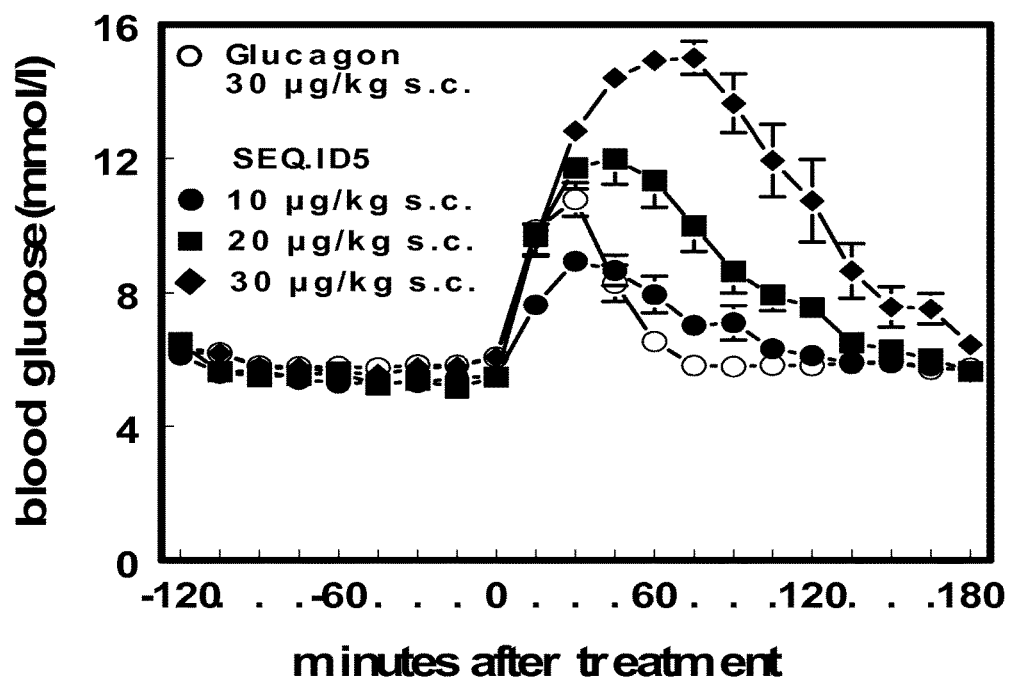

| | | |
|---|---|---|
| 7,259,234 B2 | 8/2007 | Bachovchin et al. |
| 7,265,087 B1 | 9/2007 | Göke et al. |
| 7,271,149 B2 | 9/2007 | Glaesner et al. |
| 7,297,761 B2 | 11/2007 | Beeley et al. |
| 7,312,196 B2 | 12/2007 | L'Italien et al. |
| 7,329,646 B2 | 2/2008 | Sun et al. |
| 7,399,489 B2 | 7/2008 | Kolterman et al. |
| 7,399,744 B2 | 7/2008 | Mack et al. |
| 7,407,932 B2 | 8/2008 | Young et al. |
| 7,407,955 B2 | 8/2008 | Himmelsbach et al. |
| 7,414,107 B2 | 8/2008 | Larsen |
| 7,419,952 B2 | 9/2008 | Beeley et al. |
| 7,442,680 B2 | 10/2008 | Young et al. |
| 7,442,682 B2 | 10/2008 | Kitaura et al. |
| 7,452,858 B2 | 11/2008 | Hiles et al. |
| 7,456,254 B2 | 11/2008 | Wright et al. |
| 7,476,652 B2 | 1/2009 | Brunner-Schwarz et al. |
| 7,507,714 B2 | 3/2009 | Pan et al. |
| 7,521,423 B2 | 4/2009 | Young et al. |
| 7,544,657 B2 | 6/2009 | Ebbehøj et al. |
| 7,563,871 B2 | 7/2009 | Wright et al. |
| 7,576,050 B2 | 8/2009 | Greig et al. |
| 7,585,837 B2 | 9/2009 | Shechter et al. |
| 7,592,010 B2 | 9/2009 | Rosen et al. |
| 7,595,293 B2 | 9/2009 | Engelund et al. |
| 7,595,294 B2 | 9/2009 | Nestor |
| 7,608,692 B2 | 10/2009 | Prickett et al. |
| 7,612,176 B2 | 11/2009 | Wright et al. |
| 7,632,806 B2 | 12/2009 | Juul-Mortensen et al. |
| 7,638,299 B2 | 12/2009 | Cho et al. |
| 7,682,356 B2 | 3/2010 | Alessi et al. |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,704,953 B2 | 4/2010 | Herman et al. |
| 7,713,930 B2 | 5/2010 | Brunner-Schwarz et al. |
| 7,723,471 B2 | 5/2010 | Levy et al. |
| 7,741,269 B2 | 6/2010 | Young et al. |
| 7,749,955 B2 | 7/2010 | Hansen et al. |
| 7,772,189 B2 | 8/2010 | Herman et al. |
| 7,790,681 B2 | 9/2010 | Hathaway et al. |
| 7,799,344 B2 | 9/2010 | Oberg |
| 7,799,759 B2 | 9/2010 | Rosen et al. |
| 7,803,404 B2 | 9/2010 | Hokenson et al. |
| 7,829,664 B2 | 11/2010 | Tatake et al. |
| 7,847,079 B2 | 12/2010 | Rosen et al. |
| 7,858,740 B2 | 12/2010 | Beeley et al. |
| 7,867,972 B2 | 1/2011 | Ballance et al. |
| 7,879,028 B2 | 2/2011 | Alessi et al. |
| 7,888,314 B2 | 2/2011 | Hathaway et al. |
| 7,897,560 B2 | 3/2011 | Dorwald et al. |
| 7,906,146 B2 | 3/2011 | Kolterman et al. |
| 7,928,065 B2 | 4/2011 | Young et al. |
| 7,928,186 B2 | 4/2011 | Chang |
| 7,935,786 B2 | 5/2011 | Larsen |
| 7,939,494 B2 | 5/2011 | Khan et al. |
| 7,960,341 B2 | 6/2011 | Hathaway et al. |
| 7,977,306 B2 | 7/2011 | Rosen et al. |
| 7,981,861 B2 | 7/2011 | Coolidge et al. |
| 7,989,585 B2 | 8/2011 | Dodd et al. |
| 7,994,121 B2 | 8/2011 | Bachovchin et al. |
| 7,994,122 B2 | 8/2011 | Riber et al. |
| 8,008,255 B2 | 8/2011 | Ong et al. |
| 8,012,464 B2 | 9/2011 | Rosen et al. |
| 8,026,210 B2 | 9/2011 | Young et al. |
| 8,030,273 B2 | 10/2011 | Au et al. |
| 8,039,432 B2 | 10/2011 | Bridon et al. |
| 8,057,822 B2 | 11/2011 | Prickett et al. |
| 8,071,539 B2 | 12/2011 | Rosen et al. |
| 8,076,288 B2 | 12/2011 | Levy et al. |
| 8,080,516 B2 | 12/2011 | Bridon et al. |
| 8,084,414 B2 | 12/2011 | Bridon et al. |
| 8,093,206 B2 | 1/2012 | Bridon et al. |
| 8,097,239 B2 | 1/2012 | Johnsson et al. |
| 8,097,586 B2 | 1/2012 | Lv et al. |
| 8,114,632 B2 | 2/2012 | Melarkode et al. |
| 8,114,833 B2 | 2/2012 | Pedersen et al. |
| 8,114,958 B2 | 2/2012 | Soares et al. |
| 8,114,959 B2 | 2/2012 | Juul-Mortensen |
| 8,119,648 B2 | 2/2012 | Himmelsbach et al. |
| 8,143,217 B2 | 3/2012 | Balkan et al. |
| 8,158,579 B2 | 4/2012 | Ballance et al. |
| 8,158,583 B2 | 4/2012 | Knudsen et al. |
| 8,178,495 B2 | 5/2012 | Chilkoti |
| 8,178,541 B2 | 5/2012 | Himmelsbach et al. |
| 8,197,450 B2 | 6/2012 | Glejbol et al. |
| 8,211,439 B2 | 7/2012 | Rosen et al. |
| 8,232,281 B2 | 7/2012 | Dugi et al. |
| 8,236,760 B2 | 8/2012 | Pimentel et al. |
| 8,252,739 B2 | 8/2012 | Rosen et al. |
| 8,263,545 B2 | 9/2012 | Levy et al. |
| 8,263,550 B2 | 9/2012 | Beeley et al. |
| 8,263,554 B2 | 9/2012 | Tatarkiewicz et al. |
| 8,268,781 B2 | 9/2012 | Gotthardt et al. |
| 8,278,272 B2 | 10/2012 | Greig et al. |
| 8,278,420 B2 | 10/2012 | Wang et al. |
| 8,288,338 B2 | 10/2012 | Young et al. |
| 8,293,726 B2 | 10/2012 | Habib |
| 8,293,869 B2 | 10/2012 | Bossard et al. |
| 8,293,871 B2 | 10/2012 | Wright et al. |
| 8,299,024 B2 | 10/2012 | Rabinovitch et al. |
| 8,299,025 B2 | 10/2012 | Alessi et al. |
| 8,329,419 B2 | 12/2012 | Nicolaou et al. |
| 8,329,648 B2 | 12/2012 | Fineman et al. |
| 8,338,368 B2 | 12/2012 | Dimarchi et al. |
| 8,343,910 B2 | 1/2013 | Shechter et al. |
| 8,372,804 B2 | 2/2013 | Richardson et al. |
| 8,377,869 B2 | 2/2013 | Richardson et al. |
| 8,389,473 B2 | 3/2013 | Hathaway et al. |
| 8,404,637 B2 | 3/2013 | Levy et al. |
| 8,410,047 B2 | 4/2013 | Bock et al. |
| 8,420,604 B2 | 4/2013 | Hokenson et al. |
| 8,424,518 B2 | 4/2013 | Smutney et al. |
| 8,445,647 B2 | 5/2013 | Prickett et al. |
| 8,450,270 B2 | 5/2013 | Dimarchi et al. |
| 8,454,971 B2 | 6/2013 | Day et al. |
| 8,481,490 B2 | 7/2013 | Tatarkiewicz et al. |
| 8,485,180 B2 | 7/2013 | Smutney et al. |
| 8,497,240 B2 | 7/2013 | Levy et al. |
| 8,499,757 B2 | 8/2013 | Smutney et al. |
| 8,546,327 B2 | 10/2013 | Dimarchi et al. |
| 8,551,946 B2 | 10/2013 | Dimarchi et al. |
| 8,551,947 B2 | 10/2013 | Coolidge et al. |
| 8,557,769 B2 | 10/2013 | Coskun et al. |
| 8,557,771 B2 | 10/2013 | Fan et al. |
| 8,569,481 B2 | 10/2013 | Köster et al. |
| 8,575,097 B2 | 11/2013 | Xu et al. |
| 8,580,919 B2 | 11/2013 | Bossard et al. |
| 8,598,120 B2 | 12/2013 | Soares et al. |
| 8,603,761 B2 | 12/2013 | Nicolaou et al. |
| 8,603,969 B2 | 12/2013 | Levy et al. |
| 8,614,181 B2 | 12/2013 | Juul-Mortensen et al. |
| 8,617,613 B2 | 12/2013 | Wright et al. |
| 8,636,001 B2 | 1/2014 | Smutney et al. |
| 8,641,683 B2 | 2/2014 | Glejbol et al. |
| 8,642,544 B2 | 2/2014 | Alfaro-Lopez et al. |
| 8,664,232 B2 | 3/2014 | Himmelsbach et al. |
| 8,669,228 B2 | 3/2014 | Dimarchi et al. |
| 8,673,927 B2 | 3/2014 | Dugi et al. |
| 8,697,647 B2 | 4/2014 | Levy et al. |
| 8,697,838 B2 * | 4/2014 | Dimarchi ............ A61K 9/0019 530/303 |
| 8,710,002 B2 | 4/2014 | Rothkopf |
| 8,710,181 B2 | 4/2014 | Christiansen et al. |
| 8,716,221 B2 | 5/2014 | Lv et al. |
| 8,729,018 B2 | 5/2014 | Chilkoti |
| 8,729,019 B2 | 5/2014 | Oberg et al. |
| 8,735,350 B2 | 5/2014 | Shechter et al. |
| 8,748,376 B2 | 6/2014 | Ludvigsen et al. |
| 8,759,290 B2 | 6/2014 | James |
| 8,759,295 B2 | 6/2014 | Ghosh et al. |
| 8,772,232 B2 | 7/2014 | Lau et al. |
| 8,778,872 B2 | 7/2014 | Dimarchi et al. |

(56) References Cited

U.S. PATENT DOCUMENTS

| | | |
|---|---|---|
| 8,785,396 B2 | 7/2014 | Leone-Bay et al. |
| 8,801,700 B2 | 8/2014 | Alessi et al. |
| 8,809,499 B2 | 8/2014 | Fan et al. |
| 8,816,047 B2 | 8/2014 | Levetan et al. |
| 8,841,255 B2 | 9/2014 | Chilkoti |
| 8,853,157 B2 | 10/2014 | Knudsen et al. |
| 8,853,160 B2 | 10/2014 | Greig et al. |
| 8,877,252 B2 | 11/2014 | Wright et al. |
| 8,877,709 B2 | 11/2014 | Shechter et al. |
| 8,883,449 B2 | 11/2014 | Kjeldsen et al. |
| 8,889,619 B2 | 11/2014 | Bai et al. |
| 8,900,593 B2 | 12/2014 | Day et al. |
| 8,969,288 B2 | 3/2015 | Dimarchi et al. |
| 8,969,294 B2 | 3/2015 | Bianchi et al. |
| 8,980,830 B2 | 3/2015 | Dimarchi et al. |
| 8,981,047 B2 | 3/2015 | Dimarchi et al. |
| 9,018,164 B2 | 4/2015 | Dimarchi et al. |
| 9,181,305 B2 | 11/2015 | Haack et al. |
| 2001/0011071 A1 | 8/2001 | Knudsen et al. |
| 2001/0027180 A1 | 10/2001 | Isaacs |
| 2001/0043934 A1 | 11/2001 | L'Italien et al. |
| 2002/0061838 A1 | 5/2002 | Holmquist et al. |
| 2002/0137666 A1 | 9/2002 | Beeley et al. |
| 2002/0146405 A1 | 10/2002 | Coolidge et al. |
| 2003/0036504 A1 | 2/2003 | Kolterman et al. |
| 2003/0050237 A1 | 3/2003 | Kim et al. |
| 2003/0069182 A1 | 4/2003 | Rinella et al. |
| 2003/0087820 A1 | 5/2003 | Young et al. |
| 2003/0087821 A1 | 5/2003 | Beeley et al. |
| 2003/0092606 A1 | 5/2003 | L'Italien et al. |
| 2003/0119021 A1 | 6/2003 | Koster et al. |
| 2003/0119734 A1 | 6/2003 | Flink et al. |
| 2003/0180287 A1 | 9/2003 | Gombotz et al. |
| 2003/0216287 A1 | 11/2003 | Tang |
| 2003/0220255 A1 | 11/2003 | Knudsen et al. |
| 2004/0023871 A1 | 2/2004 | Hiles et al. |
| 2004/0029784 A1 | 2/2004 | Hathaway |
| 2004/0037826 A1 | 2/2004 | Michelsen et al. |
| 2004/0038865 A1 | 2/2004 | Gelber et al. |
| 2004/0048783 A1 | 3/2004 | Brunner-Schwarz et al. |
| 2004/0097510 A1 | 5/2004 | Himmelsbach et al. |
| 2004/0209255 A1 | 10/2004 | Koster et al. |
| 2004/0209803 A1 | 10/2004 | Baron et al. |
| 2004/0242853 A1 | 12/2004 | Greig et al. |
| 2004/0266670 A9 | 12/2004 | Hiles et al. |
| 2004/0266678 A1 | 12/2004 | Beeley et al. |
| 2004/0266683 A1 | 12/2004 | Hathaway et al. |
| 2004/0266692 A1 | 12/2004 | Young et al. |
| 2005/0009742 A1 | 1/2005 | Bertilsson et al. |
| 2005/0009847 A1 | 1/2005 | Bertilsson et al. |
| 2005/0009988 A1 | 1/2005 | Harris et al. |
| 2005/0043238 A1 | 2/2005 | Young et al. |
| 2005/0059601 A1 | 3/2005 | Beeley et al. |
| 2005/0096276 A1 | 5/2005 | Coolidge et al. |
| 2005/0101537 A1 | 5/2005 | Beeley et al. |
| 2005/0106214 A1 | 5/2005 | Chen |
| 2005/0143303 A1 | 6/2005 | Quay et al. |
| 2005/0171019 A1 | 8/2005 | Young et al. |
| 2005/0186174 A1 | 8/2005 | Bossard |
| 2005/0197287 A1 | 9/2005 | Mack et al. |
| 2005/0209142 A1 | 9/2005 | Bertilsson et al. |
| 2005/0215469 A1 | 9/2005 | Beeley et al. |
| 2005/0215475 A1 | 9/2005 | Ong et al. |
| 2005/0267034 A1 | 12/2005 | Prickett et al. |
| 2005/0271702 A1 | 12/2005 | Wright et al. |
| 2005/0281879 A1 | 12/2005 | Chen et al. |
| 2006/0003918 A1 | 1/2006 | Kim et al. |
| 2006/0057137 A1 | 3/2006 | Steiness |
| 2006/0069029 A1 | 3/2006 | Kolterman et al. |
| 2006/0073182 A1 | 4/2006 | Wong et al. |
| 2006/0074012 A1 | 4/2006 | Hiles et al. |
| 2006/0079448 A1 | 4/2006 | Bertilsson et al. |
| 2006/0084605 A1 | 4/2006 | Engelund et al. |
| 2006/0094652 A1 | 5/2006 | Levy et al. |
| 2006/0094653 A1 | 5/2006 | Levy et al. |
| 2006/0110423 A1 | 5/2006 | Wright et al. |
| 2006/0135586 A1 | 6/2006 | Kozlowski et al. |
| 2006/0135747 A1 | 6/2006 | Levy et al. |
| 2006/0148713 A1 | 7/2006 | Beeley et al. |
| 2006/0165733 A1 | 7/2006 | Betz et al. |
| 2006/0171920 A1 | 8/2006 | Shechter et al. |
| 2006/0172001 A1 | 8/2006 | Ong et al. |
| 2006/0178304 A1 | 8/2006 | Juul-Mortensen et al. |
| 2006/0183677 A1 | 8/2006 | Young et al. |
| 2006/0183682 A1 | 8/2006 | Juul-Mortensen |
| 2006/0210614 A1 | 9/2006 | Quay et al. |
| 2006/0247167 A1 | 11/2006 | Schlein et al. |
| 2006/0275252 A1 | 12/2006 | Harris et al. |
| 2006/0287221 A1 | 12/2006 | Knudsen et al. |
| 2006/0293232 A1 | 12/2006 | Levy et al. |
| 2006/0293499 A1 | 12/2006 | Bentley et al. |
| 2007/0010424 A1 | 1/2007 | Pedersen et al. |
| 2007/0010656 A1 | 1/2007 | Beeley et al. |
| 2007/0014818 A1 | 1/2007 | Betz et al. |
| 2007/0021336 A1 | 1/2007 | Anderson et al. |
| 2007/0037750 A1 | 2/2007 | Young et al. |
| 2007/0049531 A1 | 3/2007 | Knudsen et al. |
| 2007/0059373 A1 | 3/2007 | Oberg |
| 2007/0059374 A1 | 3/2007 | Hokenson et al. |
| 2007/0065469 A1 | 3/2007 | Betz et al. |
| 2007/0066528 A1 | 3/2007 | Beeley et al. |
| 2007/0092482 A1 | 4/2007 | Bossard et al. |
| 2007/0129284 A1 | 6/2007 | Kjeldsen et al. |
| 2007/0166352 A1 | 7/2007 | Wright et al. |
| 2007/0196416 A1 | 8/2007 | Li et al. |
| 2007/0281940 A1 | 12/2007 | Dugi et al. |
| 2008/0045461 A1* | 2/2008 | Ewing .................... A61K 33/26 514/4.8 |
| 2008/0071063 A1 | 3/2008 | Allan et al. |
| 2008/0091176 A1 | 4/2008 | Alessi et al. |
| 2008/0119393 A1 | 5/2008 | Beeley et al. |
| 2008/0119569 A1 | 5/2008 | Wright et al. |
| 2008/0125348 A1 | 5/2008 | Wright et al. |
| 2008/0125349 A1 | 5/2008 | Wright et al. |
| 2008/0125351 A1 | 5/2008 | Wright et al. |
| 2008/0125353 A1 | 5/2008 | Hiles et al. |
| 2008/0125361 A1 | 5/2008 | Ludvigsen et al. |
| 2008/0171848 A1 | 7/2008 | Christiansen et al. |
| 2008/0176802 A1 | 7/2008 | Prickett et al. |
| 2008/0176804 A1 | 7/2008 | Mack et al. |
| 2008/0200390 A1 | 8/2008 | Prickett et al. |
| 2008/0213288 A1 | 9/2008 | Michelsen et al. |
| 2008/0214467 A1 | 9/2008 | Prickett et al. |
| 2008/0233053 A1 | 9/2008 | Gross et al. |
| 2008/0249007 A1 | 10/2008 | Lau et al. |
| 2008/0249018 A1 | 10/2008 | Kolterman et al. |
| 2008/0249089 A1 | 10/2008 | Himmelsbach et al. |
| 2008/0255159 A1 | 10/2008 | Himmelsbach et al. |
| 2008/0260838 A1 | 10/2008 | Hokenson et al. |
| 2008/0260847 A1 | 10/2008 | Wright et al. |
| 2008/0274952 A1 | 11/2008 | Soares et al. |
| 2008/0280814 A1 | 11/2008 | Ludvigsen et al. |
| 2008/0300171 A1 | 12/2008 | Balkan et al. |
| 2008/0312157 A1 | 12/2008 | Levy et al. |
| 2008/0318865 A1 | 12/2008 | Juul-Mortensen |
| 2009/0011976 A1 | 1/2009 | Ludvigsen et al. |
| 2009/0018053 A1 | 1/2009 | L'Italien et al. |
| 2009/0029913 A1 | 1/2009 | Beeley et al. |
| 2009/0035253 A1 | 2/2009 | Wright et al. |
| 2009/0036364 A1 | 2/2009 | Levy et al. |
| 2009/0043264 A1 | 2/2009 | Glejbol et al. |
| 2009/0054315 A1 | 2/2009 | Bock et al. |
| 2009/0069226 A1 | 3/2009 | Ong et al. |
| 2009/0082255 A1 | 3/2009 | Brunner-Schwarz et al. |
| 2009/0088369 A1 | 4/2009 | Steiness |
| 2009/0098130 A1 | 4/2009 | Bradshaw et al. |
| 2009/0110647 A1 | 4/2009 | Richardson et al. |
| 2009/0111749 A1 | 4/2009 | Richardson et al. |
| 2009/0137456 A1 | 5/2009 | Dimarchi et al. |
| 2009/0137466 A1 | 5/2009 | Anderson et al. |
| 2009/0163423 A1 | 6/2009 | Young et al. |
| 2009/0170750 A1 | 7/2009 | Kjeldsen et al. |
| 2009/0176704 A1 | 7/2009 | Beeley et al. |
| 2009/0180953 A1 | 7/2009 | Gotthardt et al. |

(56) References Cited

U.S. PATENT DOCUMENTS

| | | |
|---|---|---|
| 2009/0186817 A1 | 7/2009 | Ghosh et al. |
| 2009/0186819 A1 | 7/2009 | Carrier et al. |
| 2009/0203597 A1 | 8/2009 | Rabinovitch et al. |
| 2009/0203603 A1 | 8/2009 | Baron et al. |
| 2009/0215688 A1 | 8/2009 | Knudsen et al. |
| 2009/0215694 A1 | 8/2009 | Kolterman et al. |
| 2009/0221485 A1 | 9/2009 | James |
| 2009/0226431 A1 | 9/2009 | Habib |
| 2009/0232775 A1 | 9/2009 | Bertilsson et al. |
| 2009/0232807 A1 | 9/2009 | Glaesner et al. |
| 2009/0232891 A1 | 9/2009 | Gelber et al. |
| 2009/0239796 A1 | 9/2009 | Fineman et al. |
| 2009/0247463 A1 | 10/2009 | Wright et al. |
| 2009/0253625 A1 | 10/2009 | Greig et al. |
| 2009/0258818 A1 | 10/2009 | Surolia et al. |
| 2009/0264352 A1 | 10/2009 | Anderson et al. |
| 2009/0280169 A1 | 11/2009 | Leonard |
| 2009/0280170 A1 | 11/2009 | Lee et al. |
| 2009/0286716 A1 | 11/2009 | Knudsen et al. |
| 2009/0286723 A1 | 11/2009 | Levy et al. |
| 2009/0291886 A1 | 11/2009 | Ong et al. |
| 2009/0298757 A1 | 12/2009 | Bloom et al. |
| 2009/0308290 A1 | 12/2009 | Smutney et al. |
| 2009/0308391 A1 | 12/2009 | Smutney et al. |
| 2009/0308392 A1 | 12/2009 | Smutney et al. |
| 2009/0325860 A1 | 12/2009 | Constantino et al. |
| 2010/0009904 A1 | 1/2010 | Lv et al. |
| 2010/0016806 A1 | 1/2010 | Glejbol et al. |
| 2010/0022455 A1 | 1/2010 | Chilkoti |
| 2010/0029554 A1 | 2/2010 | Ghosh et al. |
| 2010/0041867 A1 | 2/2010 | Shechter et al. |
| 2010/0056451 A1 | 3/2010 | Juul-Mortensen et al. |
| 2010/0087365 A1 | 4/2010 | Cherif-Cheikh et al. |
| 2010/0099619 A1 | 4/2010 | Levy et al. |
| 2010/0137558 A1 | 6/2010 | Lee et al. |
| 2010/0152097 A1 | 6/2010 | Wright et al. |
| 2010/0152111 A1 | 6/2010 | Wright et al. |
| 2010/0168011 A1 | 7/2010 | Jennings, Jr. et al. |
| 2010/0173844 A1 | 7/2010 | Ludvigsen et al. |
| 2010/0185184 A1 | 7/2010 | Alessi et al. |
| 2010/0190699 A1 | 7/2010 | Dimarchi et al. |
| 2010/0190701 A1 | 7/2010 | Day et al. |
| 2010/0190715 A1 | 7/2010 | Schlein et al. |
| 2010/0196405 A1 | 8/2010 | Ng et al. |
| 2010/0197565 A1 | 8/2010 | Smutney et al. |
| 2010/0210505 A1 | 8/2010 | Bossard et al. |
| 2010/0216692 A1 | 8/2010 | Brunner-Schwarz et al. |
| 2010/0240586 A1 | 9/2010 | Bao et al. |
| 2010/0247661 A1 | 9/2010 | Hokenson et al. |
| 2010/0261637 A1 | 10/2010 | Spetzler et al. |
| 2010/0278924 A1 | 11/2010 | Oberg et al. |
| 2010/0292172 A1 | 11/2010 | Ghosh et al. |
| 2010/0317056 A1 | 12/2010 | Tiwari et al. |
| 2010/0317576 A1 | 12/2010 | Rothkopf |
| 2010/0331246 A1 | 12/2010 | Dimarchi et al. |
| 2011/0003004 A1 | 1/2011 | Hokenson et al. |
| 2011/0034373 A1 | 2/2011 | Coskun et al. |
| 2011/0034377 A1 | 2/2011 | Young et al. |
| 2011/0059181 A1 | 3/2011 | Hu et al. |
| 2011/0065633 A1 | 3/2011 | Dimarchi et al. |
| 2011/0065731 A1 | 3/2011 | Dugi et al. |
| 2011/0071076 A1 | 3/2011 | Beeley et al. |
| 2011/0091420 A1 | 4/2011 | Liu et al. |
| 2011/0097386 A1 | 4/2011 | Steiner et al. |
| 2011/0097751 A1 | 4/2011 | Nicolaou et al. |
| 2011/0098217 A1 | 4/2011 | Dimarchi et al. |
| 2011/0112277 A1 | 5/2011 | Kozlowski et al. |
| 2011/0118136 A1 | 5/2011 | Köster et al. |
| 2011/0123487 A1 | 5/2011 | Chilkoti |
| 2011/0129522 A1 | 6/2011 | Mevorat-Kaplan et al. |
| 2011/0136737 A1 | 6/2011 | Levy et al. |
| 2011/0152181 A1 | 6/2011 | Alsina-Fernandez et al. |
| 2011/0152182 A1 | 6/2011 | Alsina-Fernandez et al. |
| 2011/0152185 A1 | 6/2011 | Plum et al. |
| 2011/0166062 A1 | 7/2011 | Dimarchi et al. |
| 2011/0166554 A1 | 7/2011 | Alessi et al. |
| 2011/0171178 A1 | 7/2011 | Levetan et al. |
| 2011/0178014 A1 | 7/2011 | Hathaway et al. |
| 2011/0178242 A1 | 7/2011 | Harris et al. |
| 2011/0190200 A1 | 8/2011 | Dimarchi et al. |
| 2011/0195897 A1 | 8/2011 | Kajihara et al. |
| 2011/0230409 A1 | 9/2011 | Knudsen et al. |
| 2011/0237503 A1 | 9/2011 | Alsina-Fernandez et al. |
| 2011/0237510 A1 | 9/2011 | Steiner et al. |
| 2011/0245162 A1 | 10/2011 | Fineman et al. |
| 2011/0257092 A1 | 10/2011 | Dimarchi et al. |
| 2011/0263496 A1 | 10/2011 | Fineman et al. |
| 2011/0281798 A1 | 11/2011 | Kolterman et al. |
| 2011/0288003 A1 | 11/2011 | Dimarchi et al. |
| 2011/0301080 A1 | 12/2011 | Bush et al. |
| 2011/0301081 A1 | 12/2011 | Becker et al. |
| 2011/0301084 A1 | 12/2011 | Lau et al. |
| 2011/0306549 A1 | 12/2011 | Tatarkiewicz et al. |
| 2012/0004168 A1 | 1/2012 | Young et al. |
| 2012/0021978 A1 | 1/2012 | Werner et al. |
| 2012/0040899 A1 | 2/2012 | Costello et al. |
| 2012/0046222 A1 | 2/2012 | Alfaro-Lopez et al. |
| 2012/0071510 A1 | 3/2012 | Leone-Bay et al. |
| 2012/0071817 A1 | 3/2012 | Ward et al. |
| 2012/0094356 A1 | 4/2012 | Chung et al. |
| 2012/0100070 A1 | 4/2012 | Ahn et al. |
| 2012/0122783 A1 | 5/2012 | Dimarchi et al. |
| 2012/0135922 A1 | 5/2012 | Prickett et al. |
| 2012/0136318 A1 | 5/2012 | Lanin et al. |
| 2012/0148586 A1 | 6/2012 | Chou et al. |
| 2012/0149639 A1 | 6/2012 | Balkan et al. |
| 2012/0157932 A1 | 6/2012 | Glejbol et al. |
| 2012/0172295 A1 | 7/2012 | Dimarchi et al. |
| 2012/0177697 A1 | 7/2012 | Chen |
| 2012/0196795 A1 | 8/2012 | Xu et al. |
| 2012/0196796 A1 | 8/2012 | Soares et al. |
| 2012/0196802 A1 | 8/2012 | Lv et al. |
| 2012/0196804 A1 | 8/2012 | Dimarchi et al. |
| 2012/0208755 A1 | 8/2012 | Leung et al. |
| 2012/0208831 A1 | 8/2012 | Himmelsbach et al. |
| 2012/0209213 A1 | 8/2012 | Theucher |
| 2012/0225810 A1 | 9/2012 | Pedersen et al. |
| 2012/0231022 A1 | 9/2012 | Bass et al. |
| 2012/0238493 A1 | 9/2012 | Dimarchi et al. |
| 2012/0238496 A1 | 9/2012 | Fan et al. |
| 2012/0253023 A1 | 10/2012 | Levy et al. |
| 2012/0258912 A1 | 10/2012 | Bentley et al. |
| 2012/0258985 A1 | 10/2012 | Kozlowski et al. |
| 2012/0264683 A1 | 10/2012 | Coskun et al. |
| 2012/0264684 A1 | 10/2012 | Kajihara et al. |
| 2012/0276098 A1 | 11/2012 | Hamilton et al. |
| 2012/0277154 A1 | 11/2012 | Fan et al. |
| 2012/0283179 A1 | 11/2012 | Brunner-Schwarz et al. |
| 2012/0294855 A1 | 11/2012 | Van Cauter et al. |
| 2012/0295836 A1 | 11/2012 | Knudsen et al. |
| 2012/0295846 A1 | 11/2012 | Hagendorf et al. |
| 2012/0295850 A1 | 11/2012 | Tatarkiewicz et al. |
| 2012/0302501 A1 | 11/2012 | Coolidge et al. |
| 2012/0309975 A1 | 12/2012 | Colca et al. |
| 2012/0316108 A1 | 12/2012 | Chen et al. |
| 2012/0316138 A1 | 12/2012 | Colca et al. |
| 2012/0322725 A1 | 12/2012 | Dimarchi et al. |
| 2012/0322728 A1 | 12/2012 | Colca et al. |
| 2012/0329715 A1 | 12/2012 | Greig et al. |
| 2013/0005664 A1 | 1/2013 | Chilkoti |
| 2013/0023470 A1 | 1/2013 | Young et al. |
| 2013/0023471 A1 | 1/2013 | Rabinovitch et al. |
| 2013/0046245 A1 | 2/2013 | Raab et al. |
| 2013/0053350 A1 | 2/2013 | Colca et al. |
| 2013/0065826 A1 | 3/2013 | Soula et al. |
| 2013/0079277 A1 | 3/2013 | Chilkoti |
| 2013/0079278 A1 | 3/2013 | Lau et al. |
| 2013/0084277 A1 | 4/2013 | Arnold et al. |
| 2013/0085099 A1 | 4/2013 | Chilkoti |
| 2013/0085104 A1 | 4/2013 | Chilkoti |
| 2013/0089878 A1 | 4/2013 | Nicolaou et al. |
| 2013/0090286 A1 | 4/2013 | Dimarchi et al. |
| 2013/0095037 A1 | 4/2013 | Gotthardt et al. |
| 2013/0096258 A1 | 4/2013 | Bossard et al. |

(56) References Cited

U.S. PATENT DOCUMENTS

| | | | |
|---|---|---|---|
| 2013/0104887 A1 | 5/2013 | Smutney et al. |
| 2013/0116172 A1 | 5/2013 | Dimarchi et al. |
| 2013/0116175 A1 | 5/2013 | Shechter et al. |
| 2013/0118491 A1 | 5/2013 | Richardson et al. |
| 2013/0123178 A1 | 5/2013 | Dimarchi et al. |
| 2013/0123462 A1 | 5/2013 | Dimarchi et al. |
| 2013/0125886 A1 | 5/2013 | Richardson et al. |
| 2013/0130977 A1 | 5/2013 | Wright et al. |
| 2013/0137631 A1 | 5/2013 | Levy et al. |
| 2013/0137645 A1 | 5/2013 | Rosendahl |
| 2013/0142795 A1 | 6/2013 | Bai et al. |
| 2013/0156849 A1 | 6/2013 | De Fougerolles et al. |
| 2013/0157934 A1 | 6/2013 | Dimarchi et al. |
| 2013/0157953 A1 | 6/2013 | Petersen et al. |
| 2013/0164310 A1 | 6/2013 | Annathur et al. |
| 2013/0165370 A1 | 6/2013 | Bock et al. |
| 2013/0165379 A1 | 6/2013 | Kolterman et al. |
| 2013/0172274 A1 | 7/2013 | Chilkoti |
| 2013/0178411 A1 | 7/2013 | Chilkoti |
| 2013/0178415 A1 | 7/2013 | Soula et al. |
| 2013/0184203 A1 | 7/2013 | Alfaro-Lopez et al. |
| 2013/0184443 A1 | 7/2013 | Bentley et al. |
| 2013/0189365 A1 | 7/2013 | Hokenson et al. |
| 2013/0199527 A1 | 8/2013 | Smutney et al. |
| 2013/0203660 A1 | 8/2013 | Day et al. |
| 2013/0209586 A1 | 8/2013 | Hathaway et al. |
| 2013/0217622 A1 | 8/2013 | Lee et al. |
| 2013/0236974 A1 | 9/2013 | De Fougerolles |
| 2013/0237592 A1 | 9/2013 | De Fougerolles et al. |
| 2013/0237593 A1 | 9/2013 | De Fougerolles et al. |
| 2013/0237594 A1 | 9/2013 | De Fougerolles et al. |
| 2013/0244278 A1 | 9/2013 | De Fougerolles et al. |
| 2013/0244279 A1 | 9/2013 | De Fougerolles et al. |
| 2013/0245104 A1 | 9/2013 | De Fougerolles et al. |
| 2013/0245105 A1 | 9/2013 | De Fougerolles et al. |
| 2013/0245106 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0253043 A1 | 9/2013 | De Fougerolles et al. |
| 2013/0259923 A1 | 10/2013 | Bancel et al. |
| 2013/0259924 A1 | 10/2013 | Bancel et al. |
| 2013/0266640 A1 | 10/2013 | De Fougerolles et al. |
| 2013/0280206 A1 | 10/2013 | Kozlowski et al. |
| 2013/0281368 A1 | 10/2013 | Bilsky et al. |
| 2013/0281374 A1 | 10/2013 | Levy et al. |
| 2013/0284912 A1 | 10/2013 | Vogel et al. |
| 2013/0288958 A1 | 10/2013 | Lau et al. |
| 2013/0289241 A1 | 10/2013 | Bai et al. |
| 2013/0291866 A1 | 11/2013 | Smutney et al. |
| 2013/0291867 A1 | 11/2013 | Smutney et al. |
| 2013/0296236 A1 | 11/2013 | Silvestre et al. |
| 2013/0303442 A1 | 11/2013 | Levy et al. |
| 2013/0310310 A1 | 11/2013 | Liu et al. |
| 2013/0310538 A1 | 11/2013 | Chilkoti |
| 2013/0331322 A1 | 12/2013 | Young et al. |
| 2013/0336893 A1 | 12/2013 | Haack et al. |
| 2013/0338065 A1 | 12/2013 | Smutney et al. |
| 2013/0338071 A1 | 12/2013 | Knudsen et al. |
| 2013/0345134 A1 | 12/2013 | Sauerberg et al. |
| 2014/0007873 A1 | 1/2014 | Smutney et al. |
| 2014/0011732 A1 | 1/2014 | Spetzler et al. |
| 2014/0014106 A1 | 1/2014 | Smutney et al. |
| 2014/0017208 A1 | 1/2014 | Osei |
| 2014/0031281 A1 | 1/2014 | Wright et al. |
| 2014/0038891 A1 | 2/2014 | Prickett et al. |
| 2014/0056924 A1 | 2/2014 | Van Cauter |
| 2014/0066368 A1 | 3/2014 | Mack et al. |
| 2014/0083421 A1 | 3/2014 | Smutney et al. |
| 2014/0088003 A1 | 3/2014 | Wright et al. |
| 2014/0100156 A1 | 4/2014 | Haack et al. |
| 2014/0107019 A1 | 4/2014 | Erickson et al. |
| 2014/0107021 A1 | 4/2014 | Dimarchi et al. |
| 2014/0120120 A1 | 5/2014 | Woo et al. |
| 2014/0121352 A1 | 5/2014 | Shechter et al. |
| 2014/0128318 A1 | 5/2014 | Jung et al. |
| 2014/0128604 A1 | 5/2014 | Himmelsbach et al. |
| 2014/0135348 A1 | 5/2014 | Dugi et al. |
| 2014/0141467 A1 | 5/2014 | Tiwari et al. |
| 2014/0142037 A1 | 5/2014 | Yue |
| 2014/0162943 A1 | 6/2014 | Alfaro-Lopez et al. |
| 2014/0187483 A1 | 7/2014 | Steiness |
| 2014/0200183 A1 | 7/2014 | Hathaway et al. |
| 2014/0206608 A1 | 7/2014 | Haack et al. |
| 2014/0206609 A1 | 7/2014 | Haack et al. |
| 2014/0206613 A1 | 7/2014 | Rabinovitch et al. |
| 2014/0206615 A1 | 7/2014 | Knudsen et al. |
| 2014/0212419 A1 | 7/2014 | Dimarchi et al. |
| 2014/0212440 A1 | 7/2014 | Jung et al. |
| 2014/0213513 A1 | 7/2014 | Haack et al. |
| 2014/0213516 A1 | 7/2014 | Chilkoti |
| 2014/0220029 A1 | 8/2014 | Michelsen et al. |
| 2014/0220134 A1 | 8/2014 | Zierhut et al. |
| 2014/0221280 A1 | 8/2014 | Bloom |
| 2014/0221281 A1 | 8/2014 | Haack et al. |
| 2014/0221282 A1 | 8/2014 | Sun et al. |
| 2014/0227264 A1 | 8/2014 | Rabinovitch et al. |
| 2014/0235535 A1 | 8/2014 | Erickson et al. |
| 2014/0243263 A1 | 8/2014 | Rothkopf |
| 2014/0249299 A1 | 9/2014 | Levy et al. |
| 2014/0308358 A1 | 10/2014 | Oberg et al. |
| 2014/0309168 A1 | 10/2014 | Rosendahl |
| 2014/0315953 A1 | 10/2014 | Leone-Bay et al. |
| 2015/0011467 A1 | 1/2015 | Bloom et al. |
| 2015/0126440 A1 | 5/2015 | Day et al. |
| 2015/0164995 A1 | 6/2015 | Kadereit et al. |
| 2015/0164996 A1 | 6/2015 | Kadereit et al. |
| 2015/0164997 A1 | 6/2015 | Haack et al. |
| 2015/0166625 A1 | 6/2015 | Haack et al. |
| 2015/0166627 A1 | 6/2015 | Kadereit et al. |
| 2015/0216941 A1 | 8/2015 | Bley et al. |
| 2015/0232527 A1 | 8/2015 | Gong et al. |
| 2015/0315260 A1 | 11/2015 | Bossart et al. |
| 2015/0322128 A1 | 11/2015 | Bossart et al. |
| 2015/0322129 A1 | 11/2015 | Bossart et al. |
| 2015/0368311 A1 | 12/2015 | Haack et al. |
| 2016/0168225 A1 | 6/2016 | Haack et al. |
| 2016/0220643 A1 | 8/2016 | Haack et al. |
| 2016/0235855 A1 | 8/2016 | Xiong et al. |
| 2017/0008944 A1 | 1/2017 | Bossart et al. |

FOREIGN PATENT DOCUMENTS

| | | |
|---|---|---|
| CN | 101559041 | 10/2009 |
| CN | 101663317 | 3/2010 |
| CN | 101870728 | 10/2010 |
| CN | 101601646 | 3/2011 |
| CN | 102100906 | 6/2011 |
| CN | 102363633 | 2/2012 |
| CN | 102421796 | 4/2012 |
| CN | 101444618 | 6/2012 |
| CN | 102532301 | 7/2012 |
| CN | 102816244 | 12/2012 |
| CN | 102827270 | 12/2012 |
| CN | 101670096 | 1/2013 |
| CN | 103304660 | 9/2013 |
| CN | 103421094 | 12/2013 |
| CN | 103665148 | 3/2014 |
| CN | 103833841 | 6/2014 |
| CN | 103908657 | 7/2014 |
| CN | 101798588 | 10/2014 |
| CN | 102766204 | 10/2014 |
| CN | 104926934 | 9/2015 |
| EP | 1 140 145 | 7/2005 |
| EP | 0 619 322 | 12/2005 |
| EP | 1 609 478 | 12/2005 |
| EP | 1 143 989 | 12/2006 |
| EP | 1 658 856 | 3/2010 |
| EP | 1 684 793 | 9/2011 |
| EP | 1 633 391 | 10/2011 |
| EP | 2 387 989 | 11/2011 |
| EP | 1 633 390 | 1/2012 |
| EP | 2 494 983 | 9/2012 |
| EP | 2 626 368 | 8/2013 |
| EP | 2 664 374 | 11/2013 |

(56) References Cited

FOREIGN PATENT DOCUMENTS

| | | |
|---|---|---|
| EP | 1 817 048 | 2/2014 |
| EP | 2 769 990 | 8/2014 |
| JP | 2014-227368 | 12/2014 |
| KR | 10-2012-0137271 | 12/2012 |
| KR | 10-2012-0139579 | 12/2012 |
| KR | 10-2014-0018462 | 2/2014 |
| KR | 10-2014-0058104 | 5/2014 |
| KR | 10-2014-0058387 | 5/2014 |
| KR | 10-2014-0130659 | 11/2014 |
| KR | 10-2014-0133493 | 11/2014 |
| RU | 2009121626 | 2/2011 |
| WO | 1996/019229 | 6/1996 |
| WO | 1998/005351 | 2/1998 |
| WO | 1998/008871 | 3/1998 |
| WO | 1998/030231 | 7/1998 |
| WO | 1999/007404 | 2/1999 |
| WO | 1999/025727 | 5/1999 |
| WO | 1999/025728 | 5/1999 |
| WO | 1999/034822 | 7/1999 |
| WO | 1999/043708 | 9/1999 |
| WO | 1999/047160 | 9/1999 |
| WO | 1999/064061 | 12/1999 |
| WO | 2000/015224 | 3/2000 |
| WO | 2000/037098 | 6/2000 |
| WO | 2000/041546 | 7/2000 |
| WO | 2000/041548 | 7/2000 |
| WO | 2000/055119 | 9/2000 |
| WO | 2000/066629 | 11/2000 |
| WO | 2000/071175 | 11/2000 |
| WO | 2000/073331 | 12/2000 |
| WO | 2001/051078 | 7/2001 |
| WO | 2002/016309 | 2/2002 |
| WO | 2002/034285 | 5/2002 |
| WO | 2002/067989 | 9/2002 |
| WO | 2003/011892 | 2/2003 |
| WO | 2003/020201 | 3/2003 |
| WO | 2003/061362 | 7/2003 |
| WO | 2003/077851 | 9/2003 |
| WO | 2003/084563 | 10/2003 |
| WO | 2003/092581 | 11/2003 |
| WO | 2003/099314 | 12/2003 |
| WO | 2003/101395 | 12/2003 |
| WO | 2003/105888 | 12/2003 |
| WO | 2003/105897 | 12/2003 |
| WO | 2004/004779 | 1/2004 |
| WO | 2004/004780 | 1/2004 |
| WO | 2004/004781 | 1/2004 |
| WO | 2004/005342 | 1/2004 |
| WO | 2004/012672 | 2/2004 |
| WO | 2004/018468 | 3/2004 |
| WO | 2004/035623 | 4/2004 |
| WO | 2004/045592 | 6/2004 |
| WO | 2004/056313 | 7/2004 |
| WO | 2004/056317 | 7/2004 |
| WO | 2004/089280 | 10/2004 |
| WO | 2004/089985 | 10/2004 |
| WO | 2004/105781 | 12/2004 |
| WO | 2004/105790 | 12/2004 |
| WO | 2005/000222 | 1/2005 |
| WO | 2005/000360 | 1/2005 |
| WO | 2005/012347 | 2/2005 |
| WO | 2005/021022 | 3/2005 |
| WO | 2005/046716 | 5/2005 |
| WO | 2005/048989 | 6/2005 |
| WO | 2005/049061 | 6/2005 |
| WO | 2005/049069 | 6/2005 |
| WO | 2005/054291 | 6/2005 |
| WO | 2005/077072 | 8/2005 |
| WO | 2005/077094 | 8/2005 |
| WO | 2005/102293 | 11/2005 |
| WO | 2005/110425 | 11/2005 |
| WO | 2005/115437 | 12/2005 |
| WO | 2005/117584 | 12/2005 |
| WO | 2005/120492 | 12/2005 |
| WO | 2006/017688 | 2/2006 |
| WO | 2006/024275 | 3/2006 |
| WO | 2006/024631 | 3/2006 |
| WO | 2006/029634 | 3/2006 |
| WO | 2006/037811 | 4/2006 |
| WO | 2006/044531 | 4/2006 |
| WO | 2006/051103 | 5/2006 |
| WO | 2006/051110 | 5/2006 |
| WO | 2006/066024 | 6/2006 |
| WO | 2006/069388 | 6/2006 |
| WO | 2006/073890 | 7/2006 |
| WO | 2006/074600 | 7/2006 |
| WO | 2006/083254 | 8/2006 |
| WO | 2006/086769 | 8/2006 |
| WO | 2006/097535 | 9/2006 |
| WO | 2006/110887 | 10/2006 |
| WO | 2006/114396 | 11/2006 |
| WO | 2006/125763 | 11/2006 |
| WO | 2006/134340 | 12/2006 |
| WO | 2006/138572 | 12/2006 |
| WO | 2007/019331 | 2/2007 |
| WO | 2007/022123 | 2/2007 |
| WO | 2007/024700 | 3/2007 |
| WO | 2007/033316 | 3/2007 |
| WO | 2007/033372 | 3/2007 |
| WO | 2007/035665 | 3/2007 |
| WO | 2007/047834 | 4/2007 |
| WO | 2007/047922 | 4/2007 |
| WO | 2007/056362 | 5/2007 |
| WO | 2007/064691 | 6/2007 |
| WO | 2007/065156 | 6/2007 |
| WO | 2007/067964 | 6/2007 |
| WO | 2007/075534 | 7/2007 |
| WO | 2007/109354 | 9/2007 |
| WO | 2007/120899 | 10/2007 |
| WO | 2007/121411 | 10/2007 |
| WO | 2007/128761 | 11/2007 |
| WO | 2007/133778 | 11/2007 |
| WO | 2007/139941 | 12/2007 |
| WO | 2007/140284 | 12/2007 |
| WO | 2008/021133 | 2/2008 |
| WO | 2008/021560 | 2/2008 |
| WO | 2008/023050 | 2/2008 |
| WO | 2008/038147 | 4/2008 |
| WO | 2008/058461 | 5/2008 |
| WO | 2008/071972 | 6/2008 |
| WO | 2008/073448 | 6/2008 |
| WO | 2008/081418 | 7/2008 |
| WO | 2008/086086 | 7/2008 |
| WO | 2008/098212 | 8/2008 |
| WO | 2008/101017 | 8/2008 |
| WO | 2008/148839 | 12/2008 |
| WO | 2008/152403 | 12/2008 |
| WO | 2009/020802 | 2/2009 |
| WO | 2009/024015 | 2/2009 |
| WO | 2009/029847 | 3/2009 |
| WO | 2009/030771 | 3/2009 |
| WO | 2009/035540 | 3/2009 |
| WO | 2009/055740 | 4/2009 |
| WO | 2009/055742 | 4/2009 |
| WO | 2009/058662 | 5/2009 |
| WO | 2009/058734 | 5/2009 |
| WO | 2009/063072 | 5/2009 |
| WO | 2009/067268 | 5/2009 |
| WO | 2009/095479 | 8/2009 |
| WO | 2009/099763 | 8/2009 |
| WO | 2005/081619 | 9/2009 |
| WO | 2009/113099 | 9/2009 |
| WO | 2009/137078 | 11/2009 |
| WO | 2009/137080 | 11/2009 |
| WO | 2009/143014 | 11/2009 |
| WO | 2009/143285 | 11/2009 |
| WO | 2009/152477 | 12/2009 |
| WO | 2009/153960 | 12/2009 |
| WO | 2009/155257 | 12/2009 |
| WO | 2009/155258 | 12/2009 |
| WO | 2009/158704 | 12/2009 |
| WO | 2010/011439 | 1/2010 |
| WO | 2010/013012 | 2/2010 |
| WO | 2010/043566 | 4/2010 |

(56) References Cited

FOREIGN PATENT DOCUMENTS

| | | |
|---|---|---|
| WO | 2010/070251 | 6/2010 |
| WO | 2010/070252 | 6/2010 |
| WO | 2010/070253 | 6/2010 |
| WO | 2010/070255 | 6/2010 |
| WO | 2010/071807 | 6/2010 |
| WO | 2010/096052 | 8/2010 |
| WO | 2010/096142 | 8/2010 |
| WO | 2010/102148 | 9/2010 |
| WO | 2010/120476 | 10/2010 |
| WO | 2010/121559 | 10/2010 |
| WO | 2010/123290 | 10/2010 |
| WO | 2010/133675 | 11/2010 |
| WO | 2010/133676 | 11/2010 |
| WO | 2010/138671 | 12/2010 |
| WO | 2010/142665 | 12/2010 |
| WO | 2010/148089 | 12/2010 |
| WO | 2011/000095 | 1/2011 |
| WO | 2011/006497 | 1/2011 |
| WO | 2011/011675 | 1/2011 |
| WO | 2011/012718 | 2/2011 |
| WO | 2011/020319 | 2/2011 |
| WO | 2011/020320 | 2/2011 |
| WO | 2011/024110 | 3/2011 |
| WO | 2011/039096 | 4/2011 |
| WO | 2011/049713 | 4/2011 |
| WO | 2011/052523 | 5/2011 |
| WO | 2011/056713 | 5/2011 |
| WO | 2011/058082 | 5/2011 |
| WO | 2011/058083 | 5/2011 |
| WO | 2011/075393 | 6/2011 |
| WO | 2011/075514 | 6/2011 |
| WO | 2011/075623 | 6/2011 |
| WO | 2011/080103 | 7/2011 |
| WO | 2011/084453 | 7/2011 |
| WO | 2011/084456 | 7/2011 |
| WO | 2011/084459 | 7/2011 |
| WO | 2011/087671 | 7/2011 |
| WO | 2011/087672 | 7/2011 |
| WO | 2011/088837 | 7/2011 |
| WO | 2011/094337 | 8/2011 |
| WO | 2011/109784 | 9/2011 |
| WO | 2011/117415 | 9/2011 |
| WO | 2011/117416 | 9/2011 |
| WO | 2011/119657 | 9/2011 |
| WO | 2011/143208 | 11/2011 |
| WO | 2011/143209 | 11/2011 |
| WO | 2011/144751 | 11/2011 |
| WO | 2011/156407 | 11/2011 |
| WO | 2011/153965 | 12/2011 |
| WO | 2011/160630 | 12/2011 |
| WO | 2011/162830 | 12/2011 |
| WO | 2011/163012 | 12/2011 |
| WO | 2011/163272 | 12/2011 |
| WO | 2012/163473 | 12/2011 |
| WO | 2012/012352 | 1/2012 |
| WO | 2012/012460 | 1/2012 |
| WO | 2012/015975 | 2/2012 |
| WO | 2012/031518 | 3/2012 |
| WO | 2012/035139 | 3/2012 |
| WO | 2012/050923 | 4/2012 |
| WO | 2012/059762 | 5/2012 |
| WO | 2012/064892 | 5/2012 |
| WO | 2012/080471 | 6/2012 |
| WO | 2012/088116 | 6/2012 |
| WO | 2012/088157 | 6/2012 |
| WO | 2012/122535 | 9/2012 |
| WO | 2012/130015 | 10/2012 |
| WO | 2012/138941 | 10/2012 |
| WO | 2012/140647 | 10/2012 |
| WO | 2012/150503 | 11/2012 |
| WO | 2012/158965 | 11/2012 |
| WO | 2012/162547 | 11/2012 |
| WO | 2012/167744 | 12/2012 |
| WO | 2012/169798 | 12/2012 |
| WO | 2012/173422 | 12/2012 |
| WO | 2012/177443 | 12/2012 |
| WO | 2012/177444 | 12/2012 |
| WO | 2012/177929 | 12/2012 |
| WO | 2013/002580 | 1/2013 |
| WO | 2013/004983 | 1/2013 |
| WO | 2013/009545 | 1/2013 |
| WO | 2013/029279 | 3/2013 |
| WO | 2013/041678 | 3/2013 |
| WO | 2013/060850 | 5/2013 |
| WO | 2013/074910 | 5/2013 |
| WO | 2013/174478 | 5/2013 |
| WO | 2013/078500 | 6/2013 |
| WO | 2013/090648 | 6/2013 |
| WO | 2013/092703 | 6/2013 |
| WO | 2013/093720 | 6/2013 |
| WO | 2013/101749 | 7/2013 |
| WO | 2013/104861 | 7/2013 |
| WO | 2013/148871 | 10/2013 |
| WO | 2013/148966 | 10/2013 |
| WO | 2013/151663 | 10/2013 |
| WO | 2013/151664 | 10/2013 |
| WO | 2013/151665 | 10/2013 |
| WO | 2013/151666 | 10/2013 |
| WO | 2013/151667 | 10/2013 |
| WO | 2013/151668 | 10/2013 |
| WO | 2013/151669 | 10/2013 |
| WO | 2013/151670 | 10/2013 |
| WO | 2013/151671 | 10/2013 |
| WO | 2013/151672 | 10/2013 |
| WO | 2013/151736 | 10/2013 |
| WO | 2013/160397 | 10/2013 |
| WO | 2013/163162 | 10/2013 |
| WO | 2013/164484 | 11/2013 |
| WO | 2013/171135 | 11/2013 |
| WO | 2013/177565 | 11/2013 |
| WO | 2013/186240 | 12/2013 |
| WO | 2013/192130 | 12/2013 |
| WO | 2014/012069 | 1/2014 |
| WO | 2014/016300 | 1/2014 |
| WO | 2014/017843 | 1/2014 |
| WO | 2014/017845 | 1/2014 |
| WO | 2014/017849 | 1/2014 |
| WO | 2014/027253 | 2/2014 |
| WO | 2014/027254 | 2/2014 |
| WO | 2014/041195 | 3/2014 |
| WO | 2014/041375 | 3/2014 |
| WO | 2014/056872 | 4/2014 |
| WO | 2014/073842 | 5/2014 |
| WO | 2014/073845 | 5/2014 |
| WO | 2014/081872 | 5/2014 |
| WO | 2014/091316 | 6/2014 |
| WO | 2014/096145 | 6/2014 |
| WO | 2014/140222 | 9/2014 |
| WO | 2014/152460 | 9/2014 |
| WO | 2014/158900 | 10/2014 |
| WO | 2014/170496 | 10/2014 |
| WO | 2015/055801 | 4/2015 |
| WO | 2015/055802 | 4/2015 |
| WO | 2015/067716 | 5/2015 |
| WO | 2015/086728 | 6/2015 |
| WO | 2015/086729 | 6/2015 |
| WO | 2015/086730 | 6/2015 |
| WO | 2015/086731 | 6/2015 |
| WO | 2015/086732 | 6/2015 |
| WO | 2015/086733 | 6/2015 |
| WO | 2015/100876 | 7/2015 |
| WO | 2015/104314 | 7/2015 |

OTHER PUBLICATIONS

Herling et al., "Pharmacodynamic profile of a novel inhibitor of the hepatic glucose-6-phosphatase system," Am. J. Physiol. 274(6 Pt 1):G1087-93 (Jun. 1998).

Joshi et al., "The degradation pathways of glucagon in acidic solutions," Int. J. Pharm. 203(1-2):115-25 (Aug. 2000).

King et al., "A cleavage method which minimizes side reactions following Fmoc solid phase peptide synthesis," Int. J. Pept. Protein Res. 36(3):255-66 (Sep. 1990).

(56) References Cited

OTHER PUBLICATIONS

Robberecht et al., "Comparative efficacy of seven synthetic glucagon analogs, modified in position 1, 2 and/or 12, on liver and heart adenylate cyclase from rat," Peptides 7(1):109-12 (1986).
Rovó et al., "Rational design of α-helix-stabilized exendin-4 analogues," Biochemistry 53(22):3540-52 (May 2014).
Ueda et al., "Identification of glycosylated exendin-4 analogue with prolonged blood glucose-lowering activity through glycosylation scanning substitution," Bioorg. Med. Chem. Lett 20(15):4631-4 (Jun. 2010).
Unson et al., "The role of histidine-1 in glucagon action," Arch. Biochem. Biophys. 300(2):747-50 (Feb. 1993).
Extended European Search Report from the European Patent Office for European Application No. 14305935, dated Nov. 3, 2014 (4 pages).
International Search Report from International Application No. PCT/EP2015/063607, dated Sep. 23, 2015.
Written Opinion of the International Searching Authority from International Application No. PCT/EP2015/063607, dated Sep. 23, 2015.
Amylin Pharmaceuticals, Inc. (2007) "Byetta: Exenatide Injection," Product Information. Accessible on the Internet at URL: http://www.accessdata.fda.gov/drugsatfda_docs/label/2008/021773s012lbl.pdf. [Last Accessed Jun. 2, 2014].
Baggio et al. (2007) "Biology of incretins: GLP-1 and GIP," Gastroenterology. 132:2131-2157.
Bhat et al. (Jun. 1, 2013) "A novel GIP-oxyntomodulin hybrid peptide acting through GIP, glucagon and GLP-1 receptors exhibits weight reducing and anti-diabetic properties," Biochem. Pharmacol. 85:1655-1662.
Bhat et al. (Mar. 17, 2013) "A DPP-IV-resistant triple-acting agonist of GIP, GLP-1 and glucagon receptors with potent glucose-lowering and insulinotropic actions in high-fat-fed mice," Diabetologia. 56:1417-1424.
Biron et al. (2006) "Optimized selective N-methylation of peptides on solid support," J. Peptide Sci. 12:213-219.
Bis et al. (Jun. 27, 2014) "Antimicrobial preservatives induce aggregation of interferon alpha-2a: the order in which preservatives induce protein aggregation is independent of the protein," Int. J. Pharm. 472:356-361.
Braga et al. (2005) "Making Crystals from Crystals: a green route to crystal engineering and polymorphism," Chem. Commun. 2005:3635-3645.
Bunck et al. (Sep. 2011) "Effects of Exenatide on Measures of B-Cell Function After 3 Years in Metformin-Treated Patients with Type 2 Diabetes," Diabetes Care. 34:2041-2047.
Buse et al. (2009) "Liraglutide once a day versus exenatide twice a day for type 2 diabetes: a 26-week randomised, parallel group, multinational, open-label trial (LEAD-6)," The Lacenet. 374:39-47.
Chae et al. (2010) "The fatty acid conjugated exendin-4 analogs for type 2 antidiabetic therapeutics," Journal of Controlled Release. 144:10-16.
Chen et al. (Jan. 2014) "Hyaluronic acid-based drug conjugates: state-of-the-art and perspectives," J. Biomed. Nanotechnol. 10(1):4-16.
Chhabra et al. (1998) "An Appraisal of New Variants of Dde Amine Protecting Group for Solid Phase Peptide Synthesis," Tetrahedron Letters. 39:1603-1606.
Creutzfeld et al. (1978) "Gastric inhibitory polypeptide (GIP) and insulin in obesity: increased response to stimulation and defective feedback control of serum levels," Diabetologia. 14:15-24.
Day et al. (2009) "A New Glucagon and GLP-1 co-agonist Eliminates Obesity in Rodents," Nature Chemical Biology. 5(10):749-757.
Deacon (2004) "Circulation and degradation of GIP and GLP-1," Horm. Metab. Res. 36:761-765.
Druce et al. (2009) "Investigation of structure-activity relationships of Oxyntomodulin (Oxm) using Oxm analogs," Endocrinology. 150(4)1712-1722.

Drucker et al. (2010) "Liraglutide," New Reviews—Drug Discovery. 9(4):267-268.
Eng et al. (1990) "Purification and structure of exendin-3, a new pancreatic secretagogue isolated from Heloderma horridum venom," J. Biol. Chem. 265:20259-20262.
Eng et al. (1996) "Prolonged Effect of Exendin-4 on Hyperglycemia of db/db Mice," Diabetes. 45:152A. Abstract 554.
Ferry, Jr. "Diabetes Health (cont.)," MedicineNet. Accessible on the Internet at URL: http://www.onhelath.com/diabetes_health/page3.htm. [Last Accessed Aug. 22, 2013].
Ficht et al. (2008) "Solid-phase Synthesis of Peptide and Glycopeptide Thioesters through Side-Chain-Anchoring Strategies," Chem. Eur. J. 14:3620-3629.
Finan et al. (Dec. 8, 2014) "A rationally designed monomeric peptide triagonist corrects obesity and diabetes in rodents," Nat. Med. 21(1):27-36.—with supplementary information.
Finan et al. (Oct. 30, 2013) "Unimolecular Dual Incretins Maximize Metabolic Benefits in Rodents, Monkeys, and Humans," Sci. Trans. Med. 5:209RA151.
Furman (Mar. 15, 2012) "The development of Byetta (exenatide) from the venom of the Gilo monster as an anti-diabetic agent," Toxicon. 59:464-471.
Gault et al. (2007) "Chemical gastric inhibitory polypeptide receptor antagonism protects against obesity, insulin resistance, glucose intolerance and associated disturbances in mice fed high-fat and cafeteria diets," Diabetologia. 50:1752-1762.
Gault et al. (Aug. 1, 2011) "Administration of an acylated GLP-1 and GIP preparation provides added beneficial glucose-lowering and insulinotropic actions over single incretins in mice with Type 2 diabetes and obesity," Clin Sci (Lond). 121:107-117.
Gentilella et al. (2009) "Exenatide: A Review from Pharmacology to Clinical Practice," Diabetes, Obesity, and Metabolism. 11:544-556.
Göke et al. (1993) "Exendin-4 is a high potency agonist and truncated exendin-(9-39)-amide an antagonist at the glucagon-like peptide 1-(7-36)-amide receptor of insulin-secreting beta-cells," J. Biol. Chem. 268:19650-19655.
Hadji-Georgopoulos et al. (1983) "Increased gastric inhibitory polypeptide levels in patients with symptomatic postprandial hypoglycemia," J. Endocrinol. Metabol. 56(4):648-652.
Hargrove et al. (2007) "Biological Activity of AC3174, A Peptide Analog of Exendin-4," Regulatory Peptides. 141:113-119.
Heppner et al. (2010) "Glucagon regulation of energy metabolism," Physiol. Behav. 100:545-548.
Hjorth et al. (1994) "Glucagon and Glucagon-like Peptide 1: Selective Receptor Recognition via Distinct Peptide Epitopes," The Journal of Biological Chemistry. 269(48):30121-30124.
Holst (2007) "The physiology of glucagon-like peptide 1," Physiol. Rev. 87(4):1409-1439.
Kaiser et al. (1970) "Color test for detection of free terminal amino groups in the solid-phase synthesis of peptides." Anal. Biochem. 34:595-598.
Kamerzell et al. (2011) "Protein—excipient interactions: Mechanisms and biophysical characterization applied to protein formulation development," Adv. Drug Deliv. Rev. 63:1118-1159.
Kazakos et al. (2011) "Incretin effect: GLP-1, GIP, DPP4," Diabetes Res Clin Pract. 93(Suppl 1):S32-S36. et al. (2011) "Incretin effect: GLP-1, GIP, DPP4," Diabetes Res Clin Pract. 93(Suppl 1):S32-S36.
Knudsen et al. (2000) "Potent derivatives of glucagon-like peptide-1 with pharmacokinetic properties suitable for once daily administration" J. Med. Chem. 43(9):1664-1669.
Kong et al. (2010) "Long acting hyaluronate—exendin 4 conjugate for the treatment of type 2 diabetes," Biomaterials. 31:4121-4128.
Korczyn et al. (2002) "Emerging Therapies in the Pharmacological Treatment of Parkinson's Disease," Drugs. 62:775-786.
Kosinski et al. (Mar. 16, 2012) "The glucagon receptor is involved in mediating the body weight-lowering effects of oxyntomodulin," Obesity (Silver Spring). 20:1566-1571.
Krstenansky et al. (1986) "Importance of the 10-13 Region of Glucagon for Its Receptor Interaction and Activation of Adenylate Cyclase," Biochemistry. 25(13):3833-3839.

(56) References Cited

OTHER PUBLICATIONS

Lee et al. (May 10, 2013) "Hormonal Response to a Mixed-Meal Challenge After Reversal of Gastric Bypass for Hypoglycemia," J. Clin. Endocrinol. Metab. 98(7):E1208-E1212.
Li et al. (Jul.. 25, 2012) "Cloning, expressing of Exendin-4 analogue and bioactivity analysis in vivo," Chinese Journal of Biotechnology. 28(7):877-886.
Liu et al. (2011) "Solid phase peptide synthesis and analysis for exendin-4," China Biotechnology. 31(2):69-73.—English abstract and drawings.
Lorenz et al. (2013) "Recent progress and future options in the development of GLP-1 receptor agonists for the treatment of diabesity" Bioorg. Med. Chem. Lett. 23(14):4011-4018.
Lozano et al. (2013) "Polyarginine nanocapsules: a new platform for intracellular drug delivery," Journal of Nanoparticle Research. 15:1515. pp. 1-14.
Margolis (2003) "Diagnosis of Huntington Disease," Clin. Chem. 49:1726-1732.
Martin et al. (1998) "Neurodegeneration in excitotoxicity, global cerebral ischemia, and target deprivation: A perspective on the contributions of apoptosis and necrosis," Brain Res. Bull. 46:281-309.
McLaughlin et al. (2010) "Reversible Hyperinsulinemic Hypoglycemia after Gastric Bypass: A Consequence of Altered Nutrient Delivery," J. Clin. Endocrinol. Metabol. 95(4):1851-1855.
Medline Plus "Obesity," National Insitute of Health. Accessible on the Internet at URL: http://www.nlm.nih.gov/medlineplus/obesity.html. [Last Accessed Aug. 22, 2013].
Meier (Sep. 4, 2012) "GLP-1 receptor agonists for individualized treatment of type 2 diabetes mellitus," Nat. Rev. Endocrinol. 8:728-742.
Meier et al. (May 21, 2015) "Incretin-based therapies: where will we be 50 years from now?" Diabetologia. 58:1745-1750.
Miyawaki et al. (2002) "Inhibition of gastric inhibitory polypeptide signaling prevents obesity," Nat. Med. 8(7):738-742.
Murage et al. (2008) "Search for alpha-helical propensity in the receptor-bound conformation of glucagon-like peptide-1," Bioorg. Med. Chem. 16:10106-10112.
Nauck et al. (1993) "Additive insulinotropic effects of exogenous synthetic human gastric inhibitory polypeptide and glucagon-like peptide-1-(7-36) amide infused at near-physiological insulinotropic hormone and glucose concentrations," J. Clin. Endocrinol. Metab. 76:912-917.
Norris et al. (2009) "Exenatide Efficacy and Safety: A Systematic Review," Diabetic Medicine. 26:837-846.
Norwegian Institute of Public Health (Dec. 19, 2013) ATC/DDD Index for Cardiovascular System.
Oh et al. (2010) "Target specific and long-acting delivery of protein, peptide, and nucleotide therapeutics using hyaluronic acid derivatives," Journal of Controlled Release. 141:2-12.
Pan et al. (2006) "Design of a long acting peptide functioning as both a glucagon-like peptide-1 receptor agonist and a glucagon receptor antagonist." Journal of Biological Chemistry. 281(18):12506-12515.
Pedersen et al. (2006) "N- and C-terminal hydrophobic patches are involved in fibrillation of glucagon," Biochemistry. 45:14503-14512.
Pocai (2009) "Glucagon-like peptide 1/glucagon receptor dual agonism reverses obesity in mice," Diabetes. 58(10):2258-2266.
Rentier et al. (Mar. 26, 2015) "Synthesis of diastereomerically pure Lys(Nε-lipoyl) building blocks and their use in Fmoc/tBu solid phase synthesis of lipoyl-containing peptides for diagnosis of primary biliary cirrhosis," Journal of Peptide Science. 21(5):408-414.
Seddon (2004) "Pseudopolymorph: A polemic," Crystal Growth and Design. 4(6):1087.
Shiau et al. (1998) "The structural basis of estrogen receptor/coactivator recognition and the antagonism of this interaction by tamoxifen," Cell. 95(7):927-937.
St. John Providence Health System "Preventing Obesity in Children," St. John Providence Health System. Accessible on the Internet at URL: http://www.stjohnprovidence.org/HealthInfoLib/swarticle.aspx?type=85&id=P07863. [Last Accessed Aug. 22, 2013].
Tasyurek et al. (Jul. 2014) "Incretins: Their physiology and application in the treatment of diabetes mellitus," Diabetes Metab. Res. Rev. 30(5):354-371.
United Healthcare "Diabetes," United Healthcare. Accessible on the Internet at URL: http://www.uhc.com/source4women/health_topics/diabetes/relatedinformation/d0f0417b073bf110VgnVCM1000002f10b10a.htm. [Last Accessed Aug. 22, 2013].
Vippagunta et al. (2001) "Crystalline Solids," Advanced Drug Delivery Reviews. 48:3-26.
Vojkovsky (1995) "Detection of secondary amines on solid phase," Peptide Research 8:236-237.
Ward et al. (Nov. 2013) "Peptide lipidation stabilizes structure to enhance biological function," Mol. Metabol. 2(4):468-479.
World Health Organization (2007) "Prevention of Cardiovascular Disease," World Health Organization. pp. 1-86.
Yun et al. (Feb. 2012) "Solution Structure of LXXLL-related Cofactor Peptide of Orphan Nuclear Receptor FTZ-F1." Bulletin of the Korean Chemical Society, 33(2):583-588.
Stoessl et al. (2008) "Potential therapeutic targets for Parkinson's disease," Expert Opinion on Therapeutic Targets. 12(4):425-436.
Bayram et al. (Sep. 2014) "Effects of glucagon-like peptide-1 in diabetic rat small resistance arteries," Journal of Cardiovascular Pharmacology. 64(3):277-84.
Brom et al. (Feb. 1, 2014) "Non-invasive quantification of the beta cell mass by SPECT with 111In-labelled exendin," Diabetologia. 57(5):950-959.
Cai et al. (Dec. 2014) "Rb and p107 are required for alpha cell survival, beta cell cycle control and glucagon-like peptide-1 action," Diabetologia. 57(12):2555-2565.
Charokopou et al. (Nov. 2014) "Cost-effectiveness of saxagliptin compared to GLP-1 analogues as an add-on to insulin in the treatment of type 2 diabetes mellitus from a UK health care perspective," Value in Health. 17(7):A347. Abstract No. PDB89.
Chen et al. (Dec. 14, 2013) "Exendin-4 is effective against metabolic disorders induced by intrauterine and postnatal overnutrition in rodents," Diabetologia. 57(3):614-622.
Choi et al. (Jun. 2014) "A long-acting exendin-4 analog conjugate to the human fcfragment reveals low immunogenic potential," Diabetes. 63(Suppl 1):A259-A260. Abstract No. 1009-P.
Clemmensen et al. (Dec. 30, 2013) "GLP-1/glucagon coagonism restores leptin responsiveness in obese mice chronically maintained on an obesogenic diet," Diabetes. 63(4):1422-1427.
De Marinis et al. (Jun. 2014) "Differential action of GLP-1 and GIP on human pancreatic islet function and viability," Diabetes. 63(Suppl 1):A52. Abstract No. 196-OR.
De Marinis et al. (Sep. 2014) "Differential action of GLP-1 and GIP on human pancreatic islet function and viability," Diabetologia. 57(Suppl 1):S171. Abstract No. 401.
Eriksson et al. (Feb. 10, 2014) "Detection of metastatic insulinoma by positron emission tomography with [(68)ga]exendin-4—a case report," J. Clin. Endocrinol. Metab. 99(5):1519-1524.
Eriksson et al. (May 2014) "Effects of the glucagon-like peptide-1 analog exendin-4 on reendothelialization and intimal hyperplasia formation in an animal model of vascular injury," Arteriosclerosis, Thrombosis, and Vascular Biology. 34(Suppl 1): Abstract No. 515.
Gong et al. (Apr. 18, 2014) "Geniposide and its iridoid analogs exhibit antinociception by acting at the spinal GLP-1 receptors," Neuropharmacology. 84:31-45.
Gupta et al. (Sep. 25, 2014) "Mitigation of autophagy ameliorates hepatocellular damage following ischemia reperfusion injury in murine steatotic liver," Am. J. Physiol. Gastrointest. Liver Physiol. 307(11):G1088-G1099.
Jerlhag et al. (Jun. 2014) "A glucagon like peptide-1 analogue reduces alcohol intake and prevents relapse drinking," Alcoholism: Clinical and Experimental Research. 38(Suppl 1):85A. Abstract No. 0339.
Jin et al. (Jun. 24, 2014) "Dipeptidyl peptidase IV inhibitor MK-0626 attenuates pancreatic islet injury in tacrolimus-induced diabetic rats," PloS one. 9(6):e100798. pp. 1-10.

(56) References Cited

OTHER PUBLICATIONS

Johnson et al. (Sep. 5, 2014) "A Potent α/β-Peptide Analogue of GLP-1 with Prolonged Action in Vivo," Journal of the American Chemical Society. 136(37):12848-12851.
Kwon et al. (Sep. 2014) "Pharmacological evaluation of once-weekly potentials by combination of long-acting insulin with long-acting exendin4 in an animal model," Diabetologia. 57(Suppl 1):S398-S399. Abstract No. 972.
Li et al. (Apr. 2014) "Vascular protective effect of exendin-4 in experimental models of oxidative stress," Cytotherapy. 16(4 Suppl):S37-S38. Abstract No. 115.
Li et al. (Nov. 5, 2014) "Exendin-4 promotes endothelial barrier enhancement via PKA-and Epac1-dependent Rac1 activation," American Journal of Physiology. 308(2):C164-C175.
Lim et al. (Nov. 18, 2014) "Evaluation of PEGylated Exendin-4 Released from Poly (Lactic-co-Glycolic Acid) Microspheres for Antidiabetic Therapy," Journal of Pharmaceutical Sciences. 104(1):72-80.
Lovshin et al. (Oct. 2014) "Blood pressure-lowering effects of incretin-based diabetes therapies," Canadian Journal of Diabetes. 38(5):364-71.
Lynch et al. (Jun. 24, 2014) "A novel DPP IV-resistant C-terminally extended glucagon analogue exhibits weight-lowering and diabetes-protective effects in high-fat-fed mice mediated through glucagon and GLP-1 receptor activation," Diabetologia. 57(9):1927-1936.
Maas et al. (Oct. 2014) "Impact of the mTOR inhibitor Everolimus on peptide receptor radionuclide therapy in a transgenic neuroendocrine tumor mouse model," European Journal of Nuclear Medicine and Molecular Imaging. 41(Suppl 2):S529. Abstract No. P593.
Masjkur et al. (Nov. 4, 2014) "Hes3 is Expressed in the Adult Pancreatic Islet and Regulates Gene Expression, Cell Growth, and Insulin Release," The Journal of Biological Chemistry. 289(51):35503-35516.
Mondragon et al. (Aug. 13, 2014) "Divergent effects of liraglutide, exendin-4, and sitagliptin on beta-cell mass and indicators of pancreatitis in a mouse model of hyperglycaemia," PloS one. 9(8):e104873. pp. 1-9.
Nagai et al. (Sep. 2014) "Effects of sitagliptin on body fat and intrahepatic lipid content in Japanese overweight patients with type 2 diabetes," Diabetologia. 57(Suppl 1):S356. Abstract No. 876.
Patel et al. (Sep. 29, 2014) "Cannabinoid receptor 1 antagonist treatment induces glucagon release and shows an additive therapeutic effect with GLP-1 agonist in diet-induced obese mice," Canadian Journal of Physiology and Pharmacology. 92(12):975-983.
Pathak et al. (Nov. 6, 2014) "Antagonism of gastric inhibitory polypeptide (GIP) by palmitoylation of GIP analogues with N- and C-terminal modifications improves obesity and metabolic control in high fat fed mice"; Molecular and Cellular Endocrinology. 401:120-129.
Pi et al. (2014) "[Clinical research progresses on glucagon-like peptide-1 analogs in treatment of diabetes mellitus]," [Jianyan Yixue Yu Linchuang]. 11(6):830-832.—with English machine translation.
Qian et al. (Jun. 19, 2014) "Analysis of the interferences in quantitation of a site-specifically PEGylated exendin-4 analog by the Bradford method," Analytical Biochemistry. 465C:50-52.
Roed et al. (Nov. 22, 2013) "Real-time trafficking and signaling of the glucagon-like peptide-1 receptor," Mol. Cell Endocrinol. 382(2):938-949.
Russell et al. (Jun. 2014) "The novel GLP-1-GLP-2 dual agonist ZP-GG-72 increases intestinal growth and improves insulin sensitivity in DIO mice," Diabetes. 63(Suppl 1):A98. Abstract No. 374-OR.
Schattauer GmbH (Jun. 12, 2014) Meeting Abstracts of the Swiss Society of Radiology and the Swiss Society of Nuclear Medicine 2014. Nuklearmedizin. 53(2):A111-A126.
Tashiro et al. (Jan. 10, 2014) "A glucagon-like peptide-1 analog liraglutide suppresses macrophage foam cell formation and atherosclerosis," Peptides. 54:19-26.
Tweedie et al. (May 2014) "Exendin-4, a candidate treatment for the clinical management of traumatic brain injury," Brain Injury. 28(5-6):549-550. Abstract No. 0101.
Vioix et al. (Nov. 2014) "Cost-minimisation analysis of dapagliflozin compared to lixisenatide as an add-on to insulin in the treatment of type 2 diabetes mellitus from a UK health care perspective," Value in Health. 17(7):A348. Abstract No. PDB95.
Wang et al. (Jun. 2014) "Microfluidic multiplexer perifusion device for studying islet immunotoxicity," Diabetes. 63(Suppl 1):A555. Abstract No. 2181-P.
Wu et al. (May 24, 2014) "(64)Cu labeled sarcophagine exendin-4 for microPET imaging of glucagon like peptide-1 receptor expression," Theranostics. 4(8):770-777.
Xu et al. (Feb. 11, 2014) "Exendin-4 alleviates high glucose-induced rat mesangial cell dysfunction through the AMPK pathway," Cell. Physiol. Biochem. 33(2):423-432.
Xu et al. (Sep. 2014) "Insulinoma imaging with glucagon-like peptide-1 receptor targeting probe (18)F-FBEM-Cys (39)-exendin-4," Journal of Cancer Research and Clinical Oncology. 140(9):1479-1488.
Yang et al. (2014) "Design, synthesis and biological evaluation of novel peptide MC62 analogues as potential antihyperglycemic agents," European Journal of Medicinal Chemistry. 73:105-111.
Yang et al. (Jun. 2014) "Exendin-4, an analogue of glucagon-like peptide-1, attenuates hyperalgesia through serotonergic pathways in rats with neonatal colonic sensitivity," J. Physiol. Pharmacol. 65(3):349-357.
Yosida et al. (May 13, 2014) "Involvement of cAMP/EPAC/TRPM2 activation in glucose- and incretin-induced insulin secretion," Diabetes. 63(10):3394-3403.
Zhang et al. (Aug. 2014) "GLP-1 ameliorates the proliferation activity of INS-1 cells inhibited by intermittent high glucose concentrations through the regulation of cyclins," Molecular Medicine Reports. 10(2):683-688.
Aramadhaka et al. (Apr. 18, 2013) "Connectivity maps for biosimilar drug discovery in venoms: The case of Gila Monster Venom and the anti-diabetes drug Byetta®," Toxicon. 69:160-167.
Bhavsar et al. (Mar. 2013) "Evolution of exenatide as a diabetes therapeutic," Curr. Diabetes Rev. 9(2):161-193.
Gao et al. (Jun. 4, 2012) "A site-specific PEGylated analog of exendin-4 with improved pharmacokinetics and pharmacodynamics in vivo," J. Pharm. Pharmacol. 64(11):1646-1653.
Gupta (May 2013) "Glucagon-like peptide-1 analogues: An overview," Indian J. Endocrinol. Metab. 17(3):413-421.
Hou et al. (Jan. 23, 2013) "Long-term treatment with EXf, a peptide analog of Exendin-4, improves β-cell function and survival in diabetic KKAy mice," Peptides. 40:123-132.
Kim et al. (Nov. 9, 2012) "Site-specific PEGylated Exendin-4 modified with a high molecular weight trimeric PEG reduces steric hindrance and increases type 2 antidiabetic therapeutic effects," Bioconjug. Chem. 23(11):2214-2220.
Lee et al. (Oct. 17, 2013) "Decanoic acid-modified glycol chitosan hydrogels containing tightly adsorbed palmityl-acylated exendin-4 as a long-acting sustained-release anti-diabetic system," Acta Biomater. 10(2):812-820.
Parkes et al. (Dec. 12, 2012) "Discovery and development of exenatide: the first antidiabetic agent to leverage the multiple benefits of the incretin hormone, GLP-1," Expert Opin. Drug Discov. 8(2):219-244.
Qian et al. (Jul. 1, 2013) "Characterization of a site-specific PEGylated analog of exendin-4 and determination of the PEGylation site," Int. J. Pharm. 454(1):553-558.
Simonsen et al. (Jan. 11, 2013) "The C-terminal extension of exendin-4 provides additional metabolic stability when added to GLP-1, while there is minimal effect of truncating exendin-4 in anaesthetized pigs," Regul. Pept. 181:17-21.
Sun et al. (Nov. 6, 2013) "Bifunctional PEGylated exenatide-amylinomimetic hybrids to treat metabolic disorders: an example of long-acting dual hormonal therapeutics," J. Med. Chem. 56(22):9328-9341.

(56) References Cited

OTHER PUBLICATIONS

Yim et al. (Aug. 8, 2013) "Synthesis and preclinical characterization of [64Cu]NODAGA-MAL-exendin-4 with a Nε-maleoyl-L-lysyl-glycine linkage," Nucl. Med. Biol. 40(8):1006-1012.
Yue et al. (Jan. 28, 2013) "Development of a new thiol site-specific prosthetic group and its conjugation with [Cys(40)]-exendin-4 for in vivo targeting of insulinomas," Bioconjug. Chem. 24(7):1191-1200.
European Search Report corresponding to European Patent Application No. 12172010, dated Apr. 19, 2013, pp. 1-6.
European Search Report corresponding to European Patent Application No. 12306232, dated Apr. 19, 2013, pp. 1-4.
European Search Report corresponding to European Patent Application No. 12306647, dated May 22, 2013, pp. 1-6.
European Search Report corresponding to European Patent Application No. 13305222, dated Jul. 15, 2013, pp. 1-10.
European Search Report corresponding to European Patent Application No. 13306712, dated May 27, 2014, pp. 1-9.
European Search Report corresponding to European Patent Application No. 13306713, dated Jun. 12, 2014, pp. 1-11.
European Search Report corresponding to European Patent Application No. 13306714, dated May 28, 2014, pp. 1-9.
European Search Report corresponding to European Patent Application No. 13306715, dated Jun. 12, 2014, pp. 1-7.
European Search Report corresponding to European Patent Application No. 13306716, dated May 27, 2014, pp. 1-12.
European Search Report corresponding to European Patent Application No. 13306717, dated Jun. 3, 2014, pp. 1-11.
European Search Report corresponding to European Patent Application No. 14305501, dated Sep. 23, 2014, pp. 1-5.
International Preliminary Report on Patentability corresponding to International Patent Application No. PCT/EP2013/062090, dated Nov. 24, 2014, pp. 1-18.
International Preliminary Report on Patentability corresponding to International Patent Application No. PCT/EP2013/070882, dated Dec. 1, 2014, pp. 1-40.
International Preliminary Report on Patentability corresponding to International Patent Application No. PCT/EP2013/077307, dated Feb. 12, 2015, pp. 1-28.
International Preliminary Report on Patentability corresponding to International Patent Application No. PCT/EP2013/077310, dated Feb. 2, 2015, pp. 1-27.
International Preliminary Report on Patentability corresponding to International Patent Application No. PCT/EP2013/077312, dated Feb. 13, 2015, pp. 1-24.
International Preliminary Report on Patentability corresponding to International Patent Application No. PCT/EP2013/077313, dated Feb. 12, 2015, pp. 1-23.
International Preliminary Report on Patentability corresponding to International Patent Application No. PCT/EP2014/077336, dated Feb. 26, 2016, pp. 1-14.
International Preliminary Report on Patentability corresponding to International Patent Application No. PCT/EP2014/077337, dated Jun. 14, 2016, pp. 1-6.
International Preliminary Report on Patentability corresponding to International Patent Application No. PCT/EP2014/077338, dated Jun. 14, 2016, pp. 1-8.
International Preliminary Report on Patentability corresponding to International Patent Application No. PCT/EP2014/077339, dated Jun. 14, 2016, pp. 1-7.
International Preliminary Report on Patentability corresponding to International Patent Application No. PCT/EP2014/077340, dated Jun. 14, 2016, pp. 1-10.
International Preliminary Report on Patentability corresponding to International Patent Application No. PCT/EP2014/077341, dated Jun. 14, 2016, pp. 1-10.
International Search Report with Written Opinion corresponding to International Patent Application No. PCT/EP2013/070882, dated Dec. 5, 2013, pp. 1-11.
International Search Report with Written Opinion corresponding to International Patent Application No. PCT/EP2013/077307, dated Feb. 18, 2014, pp. 1-9.
International Search Report with Written Opinion corresponding to International Patent Application No. PCT/EP2013/077310, dated Feb. 18, 2014, pp. 1-9.
International Search Report with Written Opinion corresponding to International Patent Application No. PCT/EP2013/077312, dated Feb. 18, 2014, pp. 1-9.
International Search Report with Written Opinion corresponding to International Patent Application No. PCT/EP2013/077313, dated Feb. 18, 2014, pp. 1-9.
International Search Report with Written Opinion corresponding to International Patent Application No. PCT/EP2014/077336, dated Mar. 18, 2015, pp. 1-12.
International Search Report with Written Opinion corresponding to International Patent Application No. PCT/EP2014/077337, dated Apr. 1, 2015, pp. 1-11.
International Search Report with Written Opinion corresponding to International Patent Application No. PCT/EP2014/077338, dated Mar. 26, 2015, pp. 1-12.
International Search Report with Written Opinion corresponding to International Patent Application No. PCT/EP2014/077339, dated May 11, 2015, pp. 1-11.
International Search Report with Written Opinion corresponding to International Patent Application No. PCT/EP2014/077340, dated Mar. 18, 2015, pp. 1-15.
International Search Report with Written Opinion corresponding to International Patent Application No. PCT/EP2014/077341, dated Mar. 18, 2015, pp. 1-14.
International Search Report with Written Opinion corresponding to International Patent Application No. PCT/EP2015/057416, dated Jun. 22, 2015, pp. 1-10.
International Search Report with Written Opinion corresponding to International Patent Application No. PCT/EP2015/057417, dated Jun. 17, 2015, pp. 1-10.
International Search Report with Written Opinion corresponding to International Patent Application No. PCT/EP2015/057418, dated Jun. 19, 2015, pp. 1-10.
International Search Report with Written Opinion corresponding to International Patent Application No. PCT/EP2016/062496, dated Aug. 3, 2016, pp. 1-9.
International Search Report with Written Opinion corresponding to International Patent Application No. PCT/EP2016/063305, dated Oct. 4, 2016, pp. 1-16.
International Search Report with Written Opinion corresponding to International Patent Application No. PCT/EP2016/063332, dated Aug. 10, 2016, pp. 1-12.
International Search Report with Written Opinion corresponding to International Patent Application No. PCT/EP2016/063339, dated Aug. 8, 2016, pp. 1-17.
International Search Report with Written Opinion corresponding to International Patent Application No. PCT/EP2013/062090, dated Feb. 7, 2014, pp. 1-14.
Pocai (Dec. 14, 2013) "Action and therapeutic potential of oxyntomodulin," Molecular Metabolism 3:2412-51.

* cited by examiner ns.

SEQUENCE LISTING

```
<160> NUMBER OF SEQ ID NOS: 36

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Amidated C-terminus
```

```
<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 29
<212> TYPE: PRT
<213> ORGANISM: Homo sapiens

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 3
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 3

Xaa Ser Gln Gly Thr Phe Thr Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 4

Xaa Ser Gln Gly Thr Phe Thr Ser Asp Leu Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Ser
        35

<210> SEQ ID NO 5
<211> LENGTH: 39
<212> TYPE: PRT
```

```
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 5

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 6

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 7

Xaa Ser Gln Gly Thr Phe Thr Ser Asp Val Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 8
```

```
Xaa Ser Gln Gly Thr Phe Thr Ser Asp Ile Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35
```

```
<210> SEQ ID NO 9
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 9
```

```
Xaa Ser Gln Gly Thr Phe Thr Ser Asp Val Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35
```

```
<210> SEQ ID NO 10
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-Phenylglycine (Phg)

<400> SEQUENCE: 10
```

```
Xaa Ser Gln Gly Thr Phe Thr Ser Asp Xaa Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35
```

```
<210> SEQ ID NO 11
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-1-Naphthylalanine (1Nal)

<400> SEQUENCE: 11
```

```
Xaa Ser Gln Gly Thr Phe Thr Ser Asp Xaa Ser Lys Gln Leu Glu Ser
1               5                   10                  15
```

Arg Arg Ala Gln Glu Phe Ile Glu Trp Leu Leu Ala Thr Gly Pro Glu
            20                  25                  30

Ser Gly Ala Pro Pro Pro Ser
            35

<210> SEQ ID NO 12
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 12

Xaa Ser Gln Gly Thr Phe Thr Ser Asp Leu Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
            35

<210> SEQ ID NO 13
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 13

Xaa Ser Gln Gly Thr Phe Thr Ser Asp Phe Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
            35

<210> SEQ ID NO 14
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 14

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)

<400> SEQUENCE: 15

Xaa Ser Gln Gly Thr Phe Thr Ser Asp Leu Ser Lys Gln Leu Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 16

Xaa Ser Gln Gly Thr Phe Thr Ser Asp Leu Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 17

Xaa Ser Gln Gly Thr Phe Thr Ser Asp Tyr Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-2-Fluorophenylglycine (2FPhg)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 18

Xaa Ser Gln Gly Thr Phe Thr Ser Asp Xaa Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-1-Naphthylalanine (1Nal)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 19

Xaa Ser Gln Gly Thr Phe Thr Ser Asp Xaa Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)

```
<223> OTHER INFORMATION: Xaa is L-Cyclohexylglycine (Chg)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 20

Xaa Ser Gln Gly Thr Phe Thr Ser Asp Xaa Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-2-Fluorophenylglycine (2FPhg)

<400> SEQUENCE: 21

Xaa Ser Gln Gly Thr Phe Thr Ser Asp Xaa Ser Lys Gln Leu Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-1-Naphthylalanine (1Nal)

<400> SEQUENCE: 22

Xaa Ser Gln Gly Thr Phe Thr Ser Asp Xaa Ser Lys Gln Leu Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Artificial polypeptide
<220> FEATURE:
```

```
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-Cyclohexylglycine (Chg)

<400> SEQUENCE: 23

Xaa Ser Gln Gly Thr Phe Thr Ser Asp Xaa Ser Lys Gln Leu Glu Ser
 1               5                  10                  15

Arg Arg Ala Gln Asp Phe Ile Glu Trp Leu Leu Ala Thr Gly Pro Glu
             20                  25                  30

Ser Gly Ala Pro Pro Pro Ser
         35

<210> SEQ ID NO 24
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-Cyclohexylglycine (Chg)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 24

Xaa Ser Gln Gly Thr Phe Thr Ser Asp Xaa Ser Lys Gln Xaa Glu Ser
 1               5                  10                  15

Arg Arg Ala Gln Glu Phe Ile Glu Trp Leu Leu Ala Thr Gly Pro Glu
             20                  25                  30

Ser Gly Ala Pro Pro Pro Ser
         35

<210> SEQ ID NO 25
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-tert-Leucine (Tle)
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 25

Xaa Ser Gln Gly Thr Phe Thr Ser Asp Xaa Ser Lys Gln Xaa Glu Ser
 1               5                  10                  15

Arg Arg Ala Gln Glu Phe Ile Glu Trp Leu Leu Ala Thr Gly Pro Glu
             20                  25                  30

Ser Gly Ala Pro Pro Pro Ser
```

```
<210> SEQ ID NO 26
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 26

His Ser Gln Gly Thr Phe Thr Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 27

His Ser Gln Gly Thr Phe Thr Ser Asp Leu Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 28

His Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 29

His Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Thr Gly Pro Glu
            20                  25                  30
```

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 30

His Ser Gln Gly Thr Phe Thr Ser Asp Val Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 31

His Ser Gln Gly Thr Phe Thr Ser Asp Ile Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (10)..(10)
<223> OTHER INFORMATION: Xaa is L-Phenylglycine (Phg)

<400> SEQUENCE: 32

His Ser Gln Gly Thr Phe Thr Ser Asp Xaa Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (10)..(10)
<223> OTHER INFORMATION: Xaa is L-1-Naphthylalanine (1Nal)

<400> SEQUENCE: 33

His Ser Gln Gly Thr Phe Thr Ser Asp Xaa Ser Lys Gln Leu Glu Ser

```
                 1               5                  10                  15
Arg Arg Ala Gln Glu Phe Ile Glu Trp Leu Leu Ala Thr Gly Pro Glu
                    20                  25                  30

Ser Gly Ala Pro Pro Pro Ser
            35

<210> SEQ ID NO 34
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 34

His Ser Gln Gly Thr Phe Thr Ser Asp Leu Ser Lys Gln Leu Glu Ser
1               5                  10                  15

Arg Arg Ala Gln Glu Phe Ile Glu Trp Leu Leu Ala Thr Gly Pro Glu
                    20                  25                  30

Ser Gly Ala Pro Pro Pro Ser
            35

<210> SEQ ID NO 35
<211> LENGTH: 39
<212> TYPE: PRT
<213> ORGANISM: Artificial Sequence
<220> FEATURE:
<223> OTHER INFORMATION: Artificial polypeptide

<400> SEQUENCE: 35

His Ser Gln Gly Thr Phe Thr Ser Asp Leu Ser Lys Gln Leu Glu Ser
1               5                  10                  15

Arg Arg Ala Gln Asp Phe Ile Glu Trp Leu Leu Ala Thr Gly Pro Glu
                    20                  25                  30

Ser Gly Ala Pro Pro Pro Ser
            35

<210> SEQ ID NO 36
<211> LENGTH: 39
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (14)..(14)
<223> OTHER INFORMATION: Xaa is L-Norleucine (Nle)

<400> SEQUENCE: 36

His Ser Gln Gly Thr Phe Thr Ser Asp Leu Ser Lys Gln Xaa Glu Ser
1               5                  10                  15

Arg Arg Ala Gln Glu Phe Ile Glu Trp Leu Leu Ala Thr Gly Pro Glu
                    20                  25                  30

Ser Gly Ala Pro Pro Pro Ser
            35
```

EXENDIN-4 DERIVATIVES AS SELECTIVE GLUCAGON RECEPTOR AGONISTS This application claims the benefit of European Patent Application No. 14305935.0, filed on Jun. 18, 2014, the disclosure of which is explictily incorporated by reference herein.

FIELD OF THE INVENTION

The present invention relates to exendin-4 peptide analogues which activate the glucagon receptor and their medical use, for example in the treatment of severe hypoglycemia.

BACKGROUND OF THE INVENTION

Exendin-4 is a 39 amino acid peptide which is produced by the salivary glands of the Gila monster (*Heloderma suspectum*) (Eng, J. et al., J. Biol. Chem., 267:7402-05, 1992). Exendin-4 is an activator of the glucagon-like peptide-1 (GLP-1) receptor, whereas it does not activate significantly the glucagon receptor.

The amino acid sequence of exendin-4 is shown as SEQ ID NO: 1

```
HGEGTFTSDLSKQMEEEAVRLFIEWLKNGGPSSGAPPPS-NH₂
```

Glucagon is a 29-amino acid peptide which is released into the bloodstream when circulating glucose is low. Glucagon's amino acid sequence is shown as SEQ ID NO 2.

```
HSQGTFTSDYSKYLDSRRAQDFVQWLMNT-OH
```

During hypoglycemia, when blood glucose levels drop below normal, glucagon signals the liver to break down glycogen and release glucose, causing an increase of blood glucose levels to reach a normal level. Hypoglycemia is a common side effect in diabetics who are treated with insulin due to elevated blood glucose levels. Thus, glucagon's most predominant role in glucose regulation is to counteract insulin action and maintain blood glucose levels.

Glucagon has an isoelectric point of approximately 7 and is therefore only poorly soluble (<0.2 mg/ml) in the pH range of 4-8. It is well soluble (>10 mg/ml) at pH values below 3 or above 9 (Bromer, W. W., Handbook of Experimental Pharmacology, Vol 66/1, 1983). Consequently, the currently available commercial solutions of glucagon (GlucaGen® HypoKit, Glucagon emergency rescue kit) are acidic and need to be prepared freshly before use due to the chemical and biophysical instability of glucagon in solution at low pH (Joshi, A. B. et al, Int. J. Ph. Sci., 203, 115-125, 2000).

The preparation of glucagon formulations with enhanced stability compared to the commercial kit solutions are described in patent applications WO9947160, WO12059762, US2011/0097386, US2011/0237510, US2011/049713, WO12012460, WO12122535, US2012/0071817, and WO13101749, the contents of which are herein incorporated by reference.

The preparation of stabilized analogues of glucagon is described in patent applications WO14016300, WO11049713, WO07056362, WO08086086, and WO09155257, the contents of which are herein incorporated by reference.

The use of 4-Thiazolylalanine in position 1 of a synthetic peptide has been described in WO07140284 for GLP-1 receptor agonists. Conversely, 4-Thiazolylalanine in the present invention surprisingly provides highly active glucagon receptor agonists with reduced activity at the GLP-1 receptor when compared to peptides that carry the natural histidine at position 1 (native glucagon).

BRIEF SUMMARY OF THE INVENTION

Provided herein are exendin-4 analogues which potently and selectively activate the glucagon receptor and show a higher solubility at a near neutral pH and an enhanced chemical stability in solution compared to natural glucagon. All the compounds carry the artificial amino acid 4-Thiazolylalanine at position 1. This surprisingly results in a higher selectivity towards the glucagon receptor versus the GLP1 receptor when identical compounds are compared to each other differing only at position 1 (Tza in position 1 instead of His). The present invention therefore provides highly selective glucagon receptor agonists.

The invention provides a peptidic compound having the formula (I):

```
                                                          (I)
Tza-Ser-Gln-Gly-Thr-Phe-Thr-Ser-Asp-X10-Ser-Lys-

Gln-X14-Glu-Ser-Arg-Arg-Ala-Gln-X21-Phe-Ile-Glu-

Trp-Leu-Leu-Ala-X29-Gly-Pro-Glu-Ser-Gly-Ala-Pro-

Pro-Pro-Ser-R¹
```

X10 represents an amino acid residue selected from Tyr, Leu, Val, Ile, Phe, Phenylglycine, 1-Naphthylalanine, 2-Fluorophenylalanine, Cyclohexylglycine and tert-Leucine X14 represents an amino acid residue selected from Leu and Nle X21 represents an amino acid residue selected from Asp and Glu, X29 represents an amino acid residue selected from Gly and Thr, R¹ represents OH or NH₂ or a salt or solvate thereof.

The compounds of the invention are glucagon receptor agonists as determined by the observation that they are capable of stimulating intracellular cAMP formation upon binding at the receptor for glucagon. The compounds exhibit at least a relative activity of 0.1%, preferably 0.5%, more preferably 1.0% and even more preferably 10.0% compared to that of natural glucagon at the glucagon receptor.

The compounds of the invention also activate the GLP1 receptor as determined by the observation that they are capable of stimulating intracellular cAMP formation upon binding at the receptor for GLP1. The activity of a given compound of this invention (expressed by its activity relative to the activity of GLP1 at the GLP1 receptor) is below 10%, more preferably below 5% and even more preferably below 2% compared to the activity of the same compound at the glucagon receptor (expressed by its activity relative to the activity of glucagon at the glucagon receptor).

Surprisingly, it was found that peptidic compounds of the formula I with 4-Thiazolylalanine at position 1 showed increased glucagon receptor activation and increased selectivity towards the activity on the GLP-1 receptor compared to derivatives having a histidine at this position. Histidine is the naturally occurring amino acid in glucagon at position 1 and has been shown to be important for the activation mechanism of the glucagon receptor (Unson, C. G. et al, Arch. Biochem. Biophys., 300, 747-750, 1993).

Further, the compounds of the invention preferably have an enhanced solubility at acidic and/or physiological pH values, e.g., at pH 4.5 and/or at pH 7.4 at 25° C., preferably at least 0.5 mg/ml, more preferably at least 1.0 mg/ml and even more preferably at least 10.0 mg/ml.

Furthermore, the compounds of the invention preferably have a high stability when stored for 14 days at 50° C. in solution at pH 7.3 (determined by chromatographic analyses as described in the Examples). Preferably, newly formed degradation products are below 40%, more preferably below 30%, even more preferably at below 20%.

In an embodiment, the C-terminal group $R^1$ is $NH_2$.

In a further embodiment, the C-terminal group $R^1$ is OH.

A further embodiment relates to a group of compounds, wherein
- X10 represents Leu,
- X14 represents an amino acid residue selected from Leu and Nle,
- X21 represents an amino acid residue selected from Asp and Glu,
- X29 represents an amino acid residue selected from Gly and Thr,
- $R^1$ represents OH, or a salt or solvate thereof.

A further embodiment relates to a group of compounds, wherein
- X10 represents Tyr,
- X14 represents an amino acid residue selected from Leu and Nle,
- X21 represents Glu,
- X29 represents an amino acid residue selected from Gly and Thr,
- $R^1$ represents OH, or a salt or solvate thereof.

A further embodiment relates to a group of compounds, wherein
- X10 represents Val,
- X14 represents Leu,
- X21 represents Glu,
- X29 represents an amino acid residue selected from Gly and Thr,
- $R^1$ represents OH, or a salt or solvate thereof.

A further embodiment relates to a group of compounds, wherein
- X10 represents Ile,
- X14 represents an amino acid residue selected from Leu and Nle,
- X21 represents Glu,
- X29 represents Thr,
- $R^1$ represents OH, or a salt or solvate thereof.

A further embodiment relates to a group of compounds, wherein
- X10 represents 1-Naphthylalanine,
- X14 represents an amino acid residue selected from Leu and Nle,
- X21 represents an amino acid residue selected from Asp and Glu,
- X29 represents Thr,
- $R^1$ represents OH, or a salt or solvate thereof.

A further embodiment relates to a group of compounds, wherein
- X10 represents 2-Fluorophenylalanine,
- X14 represents an amino acid residue selected from Leu and Nle,
- X21 represents Asp,
- X29 represents Thr,
- $R^1$ represents OH, or a salt or solvate thereof.

A further embodiment relates to a group of compounds, wherein
- X10 represents Cyclohexylglycine,
- X14 represents an amino acid residue selected from Leu and Nle,
- X21 represents an amino acid residue selected from Asp and Glu,
- X29 represents Thr,
- $R^1$ represents OH, or a salt or solvate thereof.

A further embodiment relates to a group of compounds, wherein
- X10 represents an amino acid residue selected from Tyr, Leu, Val, Ile, Phenylglycine, 1-Naphthylalanine, 2-Fluorophenylalanine and Cyclohexylglycine,
- X14 represents Leu,
- X21 represents an amino acid residue selected from Asp and Glu,
- X29 represents an amino acid residue selected from Gly and Thr,
- $R^1$ represents OH or a salt or solvate thereof.

A further embodiment relates to a group of compounds, wherein
- X10 represents an amino acid residue selected from Tyr, Leu, Ile, Phe, 1-Naphthylalanine, Cyclohexylglycine and tert-Leucine,
- X14 represents Nle,
- X21 represents an amino acid residue selected from Asp and Glu,
- X29 represents Thr,
- $R^1$ represents OH, or a salt or solvate thereof.

A further embodiment relates to a group of compounds, wherein
- X10 represents an amino acid residue selected from Leu, Phe, 1-Naphthylalanine, 2-Fluorophenylalanine and Cyclohexylglycine,
- X14 represents an amino acid residue selected from Leu and Nle
- X21 represents Asp,
- X29 represents Thr,
- $R^1$ represents OH, or a salt or solvate thereof.

A further embodiment relates to a group of compounds, wherein
- X10 represents an amino acid residue selected from Tyr, Leu, Val, Ile, Phenylglycine, 1-Naphthylalanine, Cyclohexylglycine and tert-Leucine,
- X14 represents an amino acid residue selected from Leu and Nle
- X21 represents Glu,
- X29 represents an amino acid residue selected from Gly and Thr,
- $R^1$ represents OH, or a salt or solvate thereof.

A further embodiment relates to a group of compounds, wherein
X10 represents an amino acid residue selected from Tyr, Leu, Val, Ile, Phe, Phenylglycine, 1-Naphthylalanine, 2-Fluorophenylalanine, Cyclohexylglycine and tert-Leucine,
X14 represents an amino acid residue selected from Leu and Nle
X21 represents an amino acid residue selected from Asp and Glu,
X29 represents Thr,
$R^1$ represents OH,
or a salt or solvate thereof.

A further embodiment relates to a group of compounds, wherein
X10 represents an amino acid residue selected from Tyr, Leu and Val,
X14 represents Leu,
X21 represents Glu,
X29 represents Gly,
$R^1$ represents OH,
or a salt or solvate thereof.

Specific examples of peptidic compounds of formula (I) are the compounds of SEQ ID NO: 3-25 as well as salts or solvates thereof.

Specific examples of peptidic compounds of formula (I) are the compounds of SEQ ID NO: 3, 5, 6, 9, 15, 20, 23, 24, and 25 as well as salts or solvates thereof.

In certain embodiments, i.e. when the compound of formula (I) comprises genetically encoded amino acid residues, the invention further provides a nucleic acid (which may be DNA or RNA) encoding said compound, an expression vector comprising such a nucleic acid, and a host cell containing such a nucleic acid or expression vector.

In a further aspect, the present invention provides a composition comprising a compound of the invention in admixture with a carrier. In preferred embodiments, the composition is a pharmaceutically acceptable composition and the carrier is a pharmaceutically acceptable carrier. The compound of the invention may be in the form of a salt, e.g. a pharmaceutically acceptable salt or a solvate, e.g. a hydrate. In still a further aspect, the present invention provides a composition for use in a method of medical treatment, particularly in human medicine.

In certain embodiments, the nucleic acid or the expression vector may be used as therapeutic agents, e.g. in gene therapy.

The compounds of formula (I) are suitable for therapeutic application without an additionally therapeutically effective agent. In other embodiments, however, the compounds are used together with at least one additional therapeutically active agent, as described in "combination therapy".

Compounds of this invention and formulation thereof may primarily be used to treat hypoglycemia, increase blood glucose levels, as adjunctive therapy with insulin, but also to reduce and maintain body weight, as antidote for beta-blockers and calcium-channel blockers toxication and to induce temporary relaxation of the gastro-intestinal system for radiological uses.

DETAILED DESCRIPTION OF THE INVENTION

Definitions

The amino acid sequences of the present invention contain the conventional one letter and three letter codes for naturally occurring amino acids, as well as generally accepted three letter codes for other amino acids, such as Nle (Norleucine).

Furthermore, the following codes were used for the amino acids shown in Table 1:

| Structure | Name | Code |
|---|---|---|
| 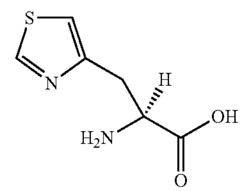 [SMILES: N[C@@H](Cc1cscn1)C(=O)O] | L-4-Thiazolylalanine | Tza |
| 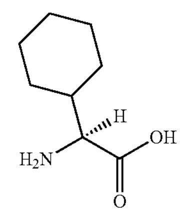 [SMILES: N[C@H](C(=O)O)C1CCCCC1] | L-Cyclohexylglycine | Chg |
| 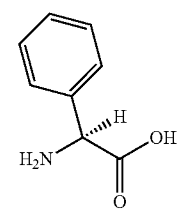 [SMILES: N[C@H](C(=O)O)c1ccccc1] | L-Phenylglycine | Phg |
| 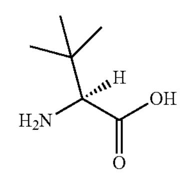 | L-tert-Leucine | Tle |
| 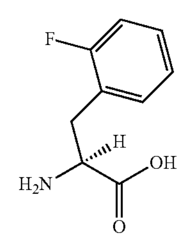 | L-2-Fluorophenylalanine | 2F-Phe |
| 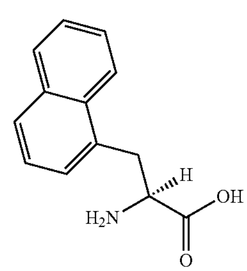 [SMILES: N[C@@H](Cc1cccc2ccccc12)C(=O)O] | L-1-Naphthylalanine | 1-Nal |

The term "native exendin-4" refers to native exendin-4 having the sequence (SEQ ID NO: 1)
HGEGTFTSDLSKQMEEEAVRLFIEWLKNGGPSSGAPPPS-NH$_2$.

The invention provides peptidic compounds as defined above.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. The peptidic compounds comprise a backbone sequence of 39 amino carboxylic acids.

For the avoidance of doubt, in the definitions provided herein, it is generally intended that the sequence of the peptidic moiety differs from native exendin-4 at least at one of those positions which are stated to allow variation. Amino acids within the peptide moiety can be considered to be numbered consecutively from 1 to 39 in the conventional N-terminal to C-terminal direction. Reference to a "position" within peptidic moiety should be constructed accordingly, as should reference to positions within native exendin-4 and other molecules, e.g., in exendin-4, His is at position 1, Gly at position 2, . . . , Met at position 14, . . . and Ser at position 39.

In a further aspect, the present invention provides a composition comprising a compound of the invention as described herein, or a salt or solvate thereof, in admixture with a carrier.

The invention also provides the use of a compound of the present invention for use as a medicament, particularly for the treatment of a condition as described herein.

The invention also provides a composition wherein the composition is a pharmaceutically acceptable composition, and the carrier is a pharmaceutically acceptable carrier.

Peptide Synthesis

The skilled person is aware of a variety of different methods to prepare peptides that are described in this invention. These methods include but are not limited to synthetic approaches and recombinant gene expression. Thus, one way of preparing these peptides is the synthesis in solution or on a solid support and subsequent isolation and purification. A different way of preparing the peptides is gene expression in a host cell in which a DNA sequence encoding the peptide has been introduced. Alternatively, the gene expression can be achieved without utilizing a cell system. The methods described above may also be combined in any way.

A preferred way to prepare the peptides of the present invention is solid phase synthesis on a suitable resin. Solid phase peptide synthesis is a well established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). Solid phase synthesis is initiated by attaching an N-terminally protected amino acid with its carboxy terminus to an inert solid support carrying a cleavable linker. This solid support can be any polymer that allows coupling of the initial amino acid, e.g. a trityl resin, a chlorotrityl resin, a Wang resin or a Rink resin in which the linkage of the carboxy group (or carboxamide for Rink resin) to the resin is sensitive to acid (when Fmoc strategy is used). The polymer support must be stable under the conditions used to deprotect the α-amino group during the peptide synthesis.

After the first amino acid has been coupled to the solid support, the α-amino protecting group of this amino acid is removed. The remaining protected amino acids are then coupled one after the other in the order represented by the peptide sequence using appropriate amide coupling reagents, for example BOP, HBTU, HATU or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc.

Finally the peptide is cleaved from the resin and deprotected. This can be achieved by using King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Potency

As used herein, the term "potency" or "in vitro potency" is a measure for the ability of a compound to activate the receptors for GLP-1 or glucagon in a cell-based assay. Numerically, it is expressed as the "EC50 value", which is the effective concentration of a compound that induces a half maximal increase of response (e.g. formation of intracellular cAMP) in a dose-response experiment.

Therapeutic Uses

The compounds of the invention are agonists of the glucagon receptor. Such agonists may at first provide therapeutic benefit to address a clinical need for targeting hypoglycemia.

Hypoglycemia induced by anti-hyperglycemic medication, e.g. insulin treatment, is an important risk in the therapy of T1 DM and T2DM to maintain glycemic control. The attempt to achieve tight glucose control can increase the risk of hypoglycemia in the outpatient and in the critical care setting. In a healthy state, fasting plasma glucose concentrations are usually above 70 mg/dL. If blood sugar levels drop below this threshold, mild hypoglycemia occurs at first with symptoms that can still be self-treated. These symptoms can include weakness, sleepiness, faintness, blurred vision or a feeling of sadness and unhappiness. Hypoglycemic symptoms also depend on the age of the patient and are predominantly neurological in older people whereas in children a change in behavior is frequently observed. Hypoglycemic events during the night can result in morning headache, poor sleep quality, vivid dreams, nightmares, profuse sweating in bed and restless behavior. Sleepwalking has also been reported during nocturnal hypoglycemia. If blood sugar levels drop even further, an event of severe hypoglycemia may be the consequence. Severe hypoglycemia is associated with a serum glucose value below 40-50 mg/dL and this event can result in neuroglycopenic symptoms such as seizure or coma which requires the assistance of a second person. Hypoglycemia can affect the brain resulting in confusion (abnormal behavior or both, such as the inability to complete routine tasks), visual disturbances, seizures and sometimes loss of consciousness. The frequent occurrence of hypoglycemia can result in reduced awareness thus increasing the risk of severe hypoglycemia significantly. Profound and prolonged severe hypoglycemia can result in death, whereas potential mechanisms responsible for hypoglycemia-induced death include brain death and cardiac arrhythmias. On average, patients with T1 DM experience 2 episodes of symptomatic hypoglycemia per week and 1 episode of severe hypoglycemia per year. The incidence of hypoglycemia in patients with T2DM treated with insulin is about one-third of that seen in T1 DM. This number may increase in patients with a longer duration of insulin treatment, the occurrence of comorbidities and the age of the patients.

The treatment of hypoglycemia depends on the duration and the intensity of the hypoglycemic event. Mild and moderate hypoglycemia can easily be self-treated by drinking or eating sugar-containing beverages or food. Severe hypoglycemia on the other hand requires the help of another person. While the intravenous application of a carbohydrate is restricted to health care professionals the administration of glucagon as a rescue medication can be carried out by any trained person either by subcutaneous or intramuscular injection. Glucagon is a peptide hormone that is produced by pancreatic alpha cells and released into the bloodstream when circulating glucose is low. As islet hormone with effects counter to those of insulin, glucagon is raising blood glucose levels by stimulating gluconeogenesis and glycogenolysis (while simultaneously inhibiting glycolysis and glycogen synthesis) to circumvent a hypoglycemic state.

Two commercial glucagon emergency kits are approved as rescue medication for severe hypoglycemia. The Glucagon Emergency Kit (Eli Lilly and Co, Indianapolis, Ind.) and the GlucaGen® Hypokit® (Novo Nordisk A/S, Bagsværd, Denmark). The kits contain a vial of glucagon powder and a syringe filled with solvent. The glucagon kit needs to be reconstituted before use. The solvent is transferred from the syringe into the vial and the vial is shaken until all solid has dissolved. The solution is then pulled back into the syringe and after removal of air bubbles in the syringe the kit is ready for administration into the leg or the abdomen. The recommended dose is 1 mg of glucagon in 1 mL of sterile water for adults and children weighing more than 25 kg and for children aged 6 to 8 or above. For children under 25 kg or younger than 6 to 8 years of age half the dose (0.5 mL) is recommended.

The FDA-approved instructions for both commercially available glucagon products allow only for immediate usage after the lyophilized powder is reconstituted in aqueous solution. Because of the complex procedure comprising different steps to solve the lyophilized powder carefully and complete an injection these products need to be administered to patients by caregivers or relatives of patients in case of an emergency situation. Based on these requirements glucagon remains an underutilized therapeutic approach despite its documented benefit to immediately improve hypoglycemia.

A glucagon receptor agonistic product with improved stability in solution, as described in this invention, could enable a ready-to-use pen device suitable for self-injection of the patient. Beyond its benefit as rescue medication such a product could offer the opportunity to become a therapy component as insulin counterpart for glucose optimization.

A distinct application may be the use in an automated closed loop artificial pancreas control system with a dual pump delivery of insulin and glucagon receptor agonist as described in this invention. Such an implantable system measures subcutaneously blood glucose and insulin is given to the patient to bring glucose levels back to a normal level. In contrast, a stabilized glucagon receptor agonist is administered by the artificial pancreas system to prevent glucose levels from going too low.

Accordingly, the compounds of the invention may be used for the treatment of mild to moderate hypoglycemia or in an event of severe hypoglycemia. Furthermore, the following forms of hypoglycemia could be treated with compounds of the invention as such are: induced by anti-diabetic treatments, e.g. insulin therapy, reactive or post-prandial hypoglycemia, fasting hypoglycemia, alcohol-induced hypoglycemia, post gastric-bypass hypoglycemia, non-diabetic hypoglycemia and pregnancy-associated hypoglycemia.

As outlined above glucagon is a hormone with acute effects counter to those of insulin, raising blood glucose levels by stimulating gluconeogenesis and glycogenolysis to circumvent a hypoglycemic state. However, recent data in rodents and humans reveal that glucagon could have also beneficial effects on energy balance, body fat mass and nutrient intake. Therefore, compounds of this invention may be used for variety of conditions or disorders beyond treatment of hypoglycemia. The compounds of this invention may be used in combination with other therapeutic active drugs. Relevant therapeutic use comprises treatment or prevention of hypoglycemia, both acute and chronic, Type 2 diabetes mellitus, delaying progression from prediabetes to type 2 diabetes, e.g. in states of impaired glucose tolerance and/or impaired fasting glucose, gestational diabetes, type 1 diabetes mellitus, obesity, diseases associated with overweight to obesity, metabolic syndrome/diabesity, cardiovascular diseases, regulation of appetite and satiety in the treatment of eating disorders, e.g. bulimia and maintaining a reduced body weight following successful weight loss.

For cases of beta-blocker poisoning where symptomatic bradycardia and hypotension are present, high-dose glucagon is considered the first-line antidote. Therefore, an injection of compounds of the current invention may be used as a defense in an overdose of beta-blockers and calcium-channel blockers.

An extra-hepatic effect of glucagon is the relaxation of smooth muscles cells in the gastrointestinal tract, comprising stomach, duodenum, small intestine, and colon. Compounds of this invention and pharmaceutical formulation thereof may be used as smooth muscle cell relaxant in combination with diagnostic imaging techniques for the gastro-intestinal tract, e.g. radiography, CT scanning, sonography, MRI imaging and nuclear medicine imaging.

Accordingly, compounds of this invention and formulation thereof may be used to treat hypoglycemia, increase blood glucose levels, as adjunctive therapy with insulin, to reduce and maintain body weight, as antidote for beta-blockers and calcium-channel blockers toxication and to induce temporary relaxation of the gastro-intestinal system for radiological uses.

Pharmaceutical Compositions

The term "pharmaceutical composition" indicates a mixture containing ingredients that are compatible when mixed and which may be administered. A pharmaceutical composition may include one or more medicinal drugs. Additionally, the pharmaceutical composition may include carriers, solvents, adjuvants, emollients, expanders, stabilizers and other components, whether these are considered active or inactive ingredients. Guidance for the skilled in preparing pharmaceutical compositions may be found, for example, in Remington: The Science and Practice of Pharmacy, (20th ed.) ed. A. R. Gennaro A. R., 2000, Lippencott Williams & Wilkins.

The exendin-4 peptide derivatives of the present invention, or salts thereof, are administered in conjunction with an acceptable pharmaceutical carrier, diluent, or excipient as part of a pharmaceutical composition. A "pharmaceutically acceptable carrier" is a carrier which is physiologically acceptable while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed.

A. R. Gennaro A. R., 2000, Lippencott Williams & Wilkins. One exemplary pharmaceutically acceptable carrier is physiological saline solution.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered parenterally.

The term "salt" or "pharmaceutically acceptable salt" means salts of the compounds of the invention which are safe and effective for use in mammals. Pharmaceutically acceptable salts may include, but are not limited to, acid addition salts and basic salts. Examples of acid addition salts include chloride, sulfate, hydrogen sulfate, (hydrogen) phosphate, acetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the compounds of the invention or salts thereof with solvent molecules, e.g. organic solvent molecules and/or water.

The term "therapeutically effective amount" of a compound refers to a nontoxic but sufficient amount of the compound to provide the desired effect. The amount of a compound of the formula (I) necessary to achieve the desired biological effect depends on a number of factors, for example the specific compound chosen, the intended use, the mode of administration and the clinical condition of the patient. An appropriate "effective" amount in any individual case may be determined by one of ordinary skill in the art using routine experimentation.

Pharmaceutical compositions of the invention are those suitable for parenteral (for example subcutaneous, intramuscular, intradermal or intravenous), oral, rectal, topical and peroral (for example sublingual) administration, although the most suitable mode of administration depends in each individual case on the nature and severity of the condition to be treated and on the nature of the compound of formula (I) used in each case.

Suitable pharmaceutical compositions may be in the form of separate units, for example capsules, tablets and powders in vials or ampoules, each of which contains a defined amount of the compound; as powders or granules; as solution or suspension in an aqueous or nonaqueous liquid; or as an oil-in-water or water-in-oil emulsion. It may be provided in single dose injectable form, for example in the form of a pen. The compositions may, as already mentioned, be prepared by any suitable pharmaceutical method which includes a step in which the active ingredient and the carrier (which may consist of one or more additional ingredients) are brought into contact.

Combination Therapy

In addition to its use as medication for hypoglycemic events, the compounds of the present invention, glucagon receptor agonists can be widely combined with other pharmacologically active compounds, such as all drugs mentioned in the Rote Liste 2014, e.g. with all antidiabetics mentioned in the Rote Liste 2014, chapter 12, all weight-reducing agents or appetite suppressants mentioned in the Rote Liste 2014, chapter 1, all lipid-lowering agents mentioned in the Rote Liste 2014, chapter 58, all antihypertensives and nephroprotectives, mentioned in the Rote Liste 2014, or all diuretics mentioned in the Rote Liste 2014, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Most of the active ingredients mentioned hereinafter are disclosed in the USP Dictionary of USAN and International Drug Names, US Pharmacopeia, Rockville 2011.

Other active substances which are suitable for such combinations include in particular those which for example add a therapeutic effect to one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargin/Lantus®, Glulisin/Apidra®, Detemir/Levemir®, Lispro/Humalog®/Liprolog®, Degludec/DegludecPlus, Aspart, basal insulin and analogues (e.g. LY2963016), PEGylated insulin Lispro (LY2605541), Humulin®, Linjeta, SuliXen®, NN1045, Insulin plus Symlin, fast-acting and short-acting insulins (e.g. Linjeta, PH20, NN1218, HinsBet), (APC-002) hydrogel, oral, inhalable, transdermal and sublingual insulins (e.g. Exubera®, Nasulin®, Afrezza, Tregopil, TPM 02, Capsulin, Oral-lyn®, Cobalamin® oral insulin, ORMD-0801, NN1953, VIAtab). Additionally included are also those insulin derivatives which are bonded to albumin or another protein by a bifunctional linker such as HM12460A (LAPS insulin). Additionally included are also those insulin derivatives which are bonded to albumin or another protein by a bifunctional linker such as HM12460A (LAPS insulin).

GLP-1, GLP-1 analogues and GLP-1 receptor agonists, for example: Lixisenatide/AVE0010/ZP10/Lyxumia, Exenatide/Exendin-4/Byetta/Bydureon/ITCA 650, Liraglutide/Victoza, Semaglutide, Taspoglutide, Albiglutide, Dulaglutide, rExendin-4, CJC-1134-PC, PB-1023, TTP-054, HM-112600, CM-3, GLP-1 Eligen, ORMD-0901, NN-9924, Nodexen, Viador-GLP-1, CVX-096, ZYOG-1, ZYD-1, MAR-701, ZP-2929, ZP-3022, CAM-2036, DA-15864, ARI-2651, ARI-2255, Exenatide-XTEN and Glucagon-Xten, MAR709, HM1525A, dual GLP1R/GlucagonR agonists, dual GLP1R/GIPR agonists, triple GLP1R/GlucagonR/GIPR agonists, combinations of GLP1R agonists with insulin derivatives such as IDegLira, Lixilan etc.

DPP-4 inhibitors, for example: Alogliptin/Nesina, Linagliptin/BI-1356/Ondero/Trajenta/Tradjenta/Trayenta/
Tradzenta, Saxagliptin/Onglyza, Sitagliptin/Januvia/Xelevia/Tesave/Janumet/Velmetia, Vildagliptin, Anagliptin, Gemigliptin, Tenegliptin, Melogliptin, Trelagliptin, DA-1229, MK-3102, KM-223.

SGLT2 inhibitors, for example: Canaglifozin, Dapaglifloxin, Remoglifoxin, Sergliflozin, Empagliflozin, Ipraglifloxin, Tofoglifloxin, luseoglifloxin, LX-4211, PF-04971729, RO-4998452, EGT-0001442, DSP-3235.

Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597), GPR40 agonists (e.g. TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK-329), inhibitors of DGAT (e.g. LCQ-908), inhibitors of protein tyrosine phosphatase 1 (e.g. Trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha2-antagonists, CCR-2 antagonists.

One or more lipid lowering agents are also suitable as combination partners, such as for example: HMG-CoA-reductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), bile acid-binding substances (e.g. Cholestyramine), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other suitable combination partners are:

Further gastrointestinal peptides such as Peptide YY 3-36 (PYY3-36) or analogues thereof, pancreatic polypeptide (PP) or analogues thereof, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the glucagon receptor. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises a compound according to the invention or a physiologically acceptable salt of such a compound and at least one of the active substances described above as combination partners, optionally together with one or more inert carriers and/or diluents.

The compound according to the invention, or physiologically acceptable salt or solvate thereof, and the additional active substance to be combined therewith may both be present together in one formulation, for example a tablet or capsule, a ready-to-use formulation in an appropriate syringe or device, a lyophilizate which can be reconstituted prior to injection or separately in two identical or different formulations, for example as so-called kit-of-parts.

LEGENDS TO THE FIGURES

FIG. 1

Blood glucose excursions after subcutaneous administration of GCG or SEQ. ID 5 in terminally anaesthetized rats. Values are mean±SEM, n=6-8 rats.

FIG. 2

Blood glucose excursions after subcutaneous administration of GCG or SEQ. ID 6 in terminally anaesthetized rats. Values are mean±SEM, n=6-8 rats.

FIG. 3

Effect of subcutaneous SEQ. ID 5 and human glucagon on blood glucose in dog

FIG. 4

Effect of subcutaneous and intramuscular SEQ. ID 5 on blood glucose in dog

FIG. 5

Effect of subcutaneous SEQ. ID 5 vs. SEQ. ID 6 on blood glucose in dog

METHODS

Abbreviations employed are as follows:
2F-Phe 2-Fluorophenylalanine
AA amino acid
cAMP cyclic adenosine monophosphate
Boc tert-butyloxycarbonyl
BOP (benzotriazol-1-yloxy)tris(dimethylamino)phosphonium hexafluorophosphate
BSA bovine serum albumin
tBu tertiary butyl
Chg Cyclohexylglycine
CTC 2-Chlorotrityl chloride
DIC N,N'-diisopropylcarbodiimide
DIPEA N,N-diisopropylethylamine
DMEM Dulbecco's modified Eagle's medium DMF dimethyl formamide
EDT ethanedithiol
FBS fetal bovine serum
Fmoc fluorenylmethyloxycarbonyl
GCG Glucagon
GLP-1 Glucagon related peptide 1
HATU 2-(1H-7-azabenzotriazol-1-yl)-1,1,3,3-tetramethyl uronium hexafluorophosphate
HBSS Hanks' Balanced Salt Solution
HBTU 2-(1H-benzotriazol-1-yl)-1,1,3,3-tetramethyl-uronium hexafluorophosphate
HEPES 2-[4-(2-hydroxyethyl)piperazin-1-yl]ethanesulfonic acid
HOBt 1-hydroxybenzotriazole
HOSu N-hydroxysuccinimide
HPLC High Performance Liquid Chromatography
HTRF Homogenous Time Resolved Fluorescence
IBMX 3-isobutyl-1-methylxanthine
Nal 1-Naphthylalanine
PBS phosphate buffered saline
PEG polyethylene glycole
Phg Phenylglycine
RP-HPLC reversed-phase high performance liquid chromatography
s.c. subcutaneous
TFA trifluoroacetic acid
Tle tert-Leucine
TRIS Tris(hydroxymethyl)-aminomethan
Trt trityl
Tza 4-Thiazolylalanine
UV ultraviolet
General Synthesis of Peptidic Compounds
Materials:

For solid phase peptide synthesis preloaded Fmoc-Ser(tBu)-Wang resin was used. Fmoc-Ser(tBu)-Wang resin was purchased from Novabiochem with a loading of 0.3 mmol/g.

Fmoc protected natural amino acids were purchased from Protein Technologies Inc., Senn Chemicals, Merck Biosciences, Novabiochem, Iris Biotech or Bachem.

The following standard amino acids were used throughout the syntheses: Fmoc-L-Ala-OH, Fmoc-L-Arg(Pbf)-OH, Fmoc-L-Asn(Trt)-OH, Fmoc-L-Asp(OtBu)-OH, Fmoc-L-Gln(Trt)-OH, Fmoc-L-Glu(OtBu)-OH, Fmoc-L-Gly-OH, Fmoc-L-His(Trt)-OH, Fmoc-L-Ile-OH, Fmoc-L-Leu-OH, Fmoc-L-Lys(Boc)-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

In addition, the following special amino acids were purchased from the same suppliers as above: Fmoc-L-Tza-OH, Fmoc-L-Phg-OH, Fmoc-L-Nal-OH, Fmoc-L-2F-Phe-OH, Fmoc-L-Chg-OH, Fmoc-L-Tle-OH The solid phase peptide syntheses were performed on a Prelude Peptide Synthesizer (Protein Technologies Inc) using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF. 2× for 20 min. Washes: 5×DMF.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analyzed by analytical HPLC and checked by ESI mass spectrometry. Crude peptides were purified by a conventional preparative RP-HPLC purification procedure.
General Preparative HPLC Purification Procedure:

The crude peptides were purified either on an Akta Purifier System or on a Jasco semiprep HPLC System. Preparative RP-C18-HPLC columns of different sizes and with different flow rates were used depending on the amount of crude peptide to be purified. Acetonitrile+0.1% TFA (B) and water+0.1% TFA (A) were employed as eluents. Product-containing fractions were collected and lyophilized to obtain the purified product, typically as TFA salt.
Solubility and Stability Testing of Exendin-4 Derivatives:

Prior to the testing of solubility and stability of a peptide batch, its content was determined. Therefore, two parameters were investigated, its purity (HPLC-UV) and the amount of salt load of the batch (ion chromatography).

For solubility testing, the target concentration was 10 mg/mL pure compound. Therefore, solutions from solid samples were prepared in different buffer systems with a concentration of 10 mg/mL compound based on the previously determined content. HPLC-UV was performed after 2 h of gentle agitation from the supernatant, which was obtained by 20 min of centrifugation at 4000 rpm.

The solubility was then determined by comparison with the UV peak areas obtained with a stock solution of the peptide at a concentration of 2 mg/mL in pure water or a variable amount of acetonitrile (optical control that all of the compound was dissolved).

For solubility testing, analytical Chromatography was performed with a Waters UPLC system on a Waters ACQUITY UPLC® CSH™ C18 1.7 μm (150×2.1 mm) at 50° C. with a gradient elution at a flow rate of 0.5 mL/min and monitored at 210-225 nm. The gradients were set up as 20% B (0-3 min) to 75% B (3-23 min) followed by a wash step at 98% B (23.5-30.5) and a equilibration period (31-37 min at 20% B). Buffer A=0.5% trifluoroacetic acid in water and B=0.35%) trifluoroacetic acid in acetonitrile. Optionally, the LC was coupled to an Waters LCT Premier ESI-TOF mass spectrometer using the positive ion mode.

For stability testing, the target concentration was 1.0 mg/mL pure compound in a pH 7.3 TRIS buffer (50 mM) containing m-cresol (30 mM), sodium chloride (85 mM) and polysorbate 20 (8 μM). The solution was stored for 14 days at 50° C. After that time, the solution was analysed by UPLC.

For stability testing, UPLC was performed on an Waters Acquity UPLC H-Class system with a Waters Acquity UPLC BEH130 C18 1.7 μm column (2.1×100 mm) at 40° C. with a gradient elution at a flow rate of 0.5 mL/min and monitored at 215 and 280 nm. The gradients were set up as 10% B to 90% B over 19.2 min and then 90% B for 0.8 min. Buffer A=0.1% formic acid in water and B=0.1% formic acid in acetonitrile.

For determination of the amount of the remaining peptide, the peak areas of the target compound at t0 and t14 were compared, resulting in "% Remaining peptide", following the equation $$\% \text{ Remaining peptide} = [(\text{peak area peptide } t14) \times 100] / \text{peak area peptide } t0.$$

The "% Normalized purity" is defined by the % Relative purity at day 14 in relation to the % Relative purity at t0 following the equation $$\% \text{ Normalized purity} = [(\% \text{ Relative purity } t14) \times 100] / \% \text{ Relative purity } t0$$

The % Relative purity at t0 was calculated by dividing the peak are of the peptide at t0 by the sum of all peak areas at t0 following the equation $$\% \text{ Relative purity } t0 = [(\text{peak area } t0) \times 100] / \text{sum of all peak areas } t0$$

Likewise, the % relative purity t14 was calculated by dividing the peak are of the peptide at t14 by the sum of all peak areas at t14 following the equation % Relative purity t14=[(peak area t14)×100]/sum of all peak areas t14

The potential difference between "% Normalized purity" and "% Remaining peptide" reflects the amount of peptide which did not remain soluble upon stress conditions.

This precipitate includes non-soluble degradation products, polymers and/or fibrils, which have been removed prior to analysis by centrifugation.

Anion Chromatography:

Instrument: Dionex ICS-2000, pre/column: Ion Pac AG-18 2×50 mm (Dionex)/AS18 2×250 mm (Dionex), eluent: aqueous sodium hydroxide, flow: 0.38 mL/min, gradient: 0-6 min: 22 mM KOH, 6-12 min: 22-28 mM KOH, 12-15 min: 28-50 mM KOH, 15-20 min: 22 mM KOH, suppressor: ASRS 300 2 mm, detection: conductivity.

In Vitro Cellular Assays for Glucagon Receptor Efficacy:

Agonism of compounds for the respective receptor was determined by functional assays measuring cAMP response of HEK-293 cell lines stably expressing human GLP-1 or glucagon receptor.

cAMP content of cells was determined using a kit from Cisbio Corp. (cat. no. 62AM4PEC) based on HTRF (Homogenous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 µl-aliquots dispensed into the wells of 96-well plates. For measurement, 25 µl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

Blood Glucose Profile in Anesthetized Rats:

The method aimed to study a test compound on the process of hepatic glycogenolysis. The rats had free access to food until the start of the experiment. It can be stated that the rise of blood glucose after administration of glucagon (GCG) or GCG-mimetic, and which lasted for about 60 to 90 minutes, was the result of the GCG- or GCG-mimetic-induced breakdown of hepatic glycogen. The effect of GCG-mimetic on hepatic glycogenolysis and the subsequent hyperglycemic peak in the blood was compared to the effect obtained with a subcutaneous bolus injection of GCG at a dose of 30 µg/kg.

Blood glucose levels were assayed in anaesthetized male Wistar rats as described previously (Herling et al. Am J Physiol. 1998; 274:G1087-93). Rats were anaesthetized with an intraperitoneal injection of pentobarbital sodium (60 mg/kg) and ketamine (10 mg/kg) and tracheotomized. Anesthesia was maintained for up to 5 hours by subcutaneous infusion of pentobarbital sodium (adjusted to the anesthetic depth of the individual animal; about 24 mg/kg/h). Body temperature was monitored with a rectal probe thermometer, and temperature was maintained at 37° C. by means of a heated surgical table. Blood samples for glucose analysis (10 µl) were obtained from the tip of the tail every 15 minutes. The rats were allowed to stabilize their blood glucose levels after surgery for up to 2 hours. Then, GCG as reference compound, or the test compound were administered subcutaneously. For GCG a dose of 30 µg/kg was used to induce hepatic glycogenolysis. The test compound SEQ. ID 5 was administered in doses of 10, 20 and 30 µg/kg, and the test compound SEQ. ID 6 was administered in doses of 10 and 30 µg/kg.

Blood Glucose Profile in Normoglycemic Beagle Dogs:

Male normoglycemic Beagle dogs were fasted overnight before and during the entire experiment. The animals were randomized to groups of n=6 per group. At time point 0 min the animals were treated with single doses of the test compound or native human glucagon as reference compound. The injection solutions were prepared freshly prior to the experiment. The test compound was administered as a single injection via three different routes (s.c., i.m. and i.v.) at doses of 1-100 µg/kg. Blood sampling is performed consecutively via puncture of the jugular vein (vena jugularis) before drug administration (=0 min) and thereafter up to 240 min. Blood glucose was determined enzymatically (hexokinase method) from whole blood, insulin was analyzed from K-EDTA plasma with a dog-specific ELISA assay.

EXAMPLES

The invention is further illustrated by the following examples.

Example 1

Synthesis of SEQ ID NO: 25

The solid phase synthesis was carried out on preloaded Fmoc-Ser(tBu)-Wang resin. The Fmoc-synthesis strategy was applied with HBTU/DIPEA-activation. In position 1 Fmoc-Tza-OH and in position 10 Fmoc-Tle-OH were used in the solid phase synthesis protocol. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 2

Synthesis of SEQ ID NO: 24

The solid phase synthesis was carried out on preloaded Fmoc-Ser(tBu)-Wang resin. The Fmoc-synthesis strategy was applied with HBTU/DIPEA-activation. In position 1 Fmoc-Tza-OH and in position 10 Fmoc-Chg-OH were used in the solid phase synthesis protocol. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 3

Synthesis of SEQ ID NO: 5

The solid phase synthesis was carried out on preloaded Fmoc-Ser(tBu)-Wang resin. The Fmoc-synthesis strategy was applied with HBTU/DIPEA-activation. In position 1 Fmoc-Tza-OH was used in the solid phase synthesis protocol. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

In an analogous way, the peptides SEQ ID NO: 3-36 were synthesized, see table 2.

TABLE 2 list of synthesized peptides and comparison of calculated vs. found molecular weight.

| SEQ ID | calc. mass | found mass |
| --- | --- | --- |
| 3 | 4259.68 | 4259.3 |
| 4 | 4229.66 | 4229.8 |
| 5 | 4279.67 | 4279.7 |
| 6 | 4323.73 | 4323.6 |
| 7 | 4259.68 | 4259.8 |
| 8 | 4273.71 | 4273.7 |
| 9 | 4215.63 | 4216.0 |
| 10 | 4293.70 | 4295.1 |
| 11 | 4357.80 | 4358.2 |
| 12 | 4273.71 | 4272.8 |
| 13 | 4293.70 | 4293.7 |
| 14 | 4273.71 | 4274.3 |
| 15 | 4259.68 | 4259.7 |
| 16 | 4273.71 | 4273.4 |
| 17 | 4323.73 | 4323.4 |
| 18 | 4311.69 | 4311.3 |
| 19 | 4343.70 | 4343.3 |
| 20 | 4293.70 | 4293.5 |
| 21 | 4311.69 | 4311.4 |
| 22 | 4343.76 | 4343.4 |
| 23 | 4285.72 | 4285.2 |
| 24 | 4299.69 | 4299.0 |
| 25 | 4273.65 | 4273.0 |
| 26 | 4242.64 | 4242.5 |
| 27 | 4212.61 | 4212.5 |
| 28 | 4262.56 | 4262.2 |
| 29 | 4306.68 | 4306.6 |
| 30 | 4242.64 | 4240.1 |
| 31 | 4256.66 | 4256.5 |
| 32 | 4276.65 | 4276.2 |
| 33 | 4340.75 | 4340.2 |
| 34 | 4256.66 | 4256.6 |
| 35 | 4242.64 | 4242.5 |
| 36 | 4256.66 | 4254.1 |

Example 4

Chemical Stability and Solubility

Solubility and chemical stability of peptidic compounds were assessed as described in Methods. The results are given in Table 3.

TABLE 3

Chemical stability and solubility

| SEQ ID | Solubility (pH7.4) [mg/ml] | Stability (pH7.3, 50° C., 2 w) [% NormalizedPurity] | Stability (pH7.3, 50° C., 2 w) [% Remaining Peptide] |
| --- | --- | --- | --- |
| 2 | <0.2 | 70 | n/a |
| 1 | >10.0 | 37 | 33 |
| 3 | >10.0 | 94 | 92 |
| 6 | >10.0 | 92 | 94 |
| 5 | >10.0 | 96 | 88 |
| 9 | >10.0 | 83 | 70 |
| 15 | >10.0 | 86 | 75 |
| 20 | >10.0 | 90 | 90 |
| 23 | >10.0 | 94 | 92 |
| 24 | >10.0 | 95 | 90 |
| 25 | >10.0 | 89 | 82 |

Example 5

In Vitro Data on GLP-1 and Glucagon Receptor

Potencies of peptidic compounds at the GLP-1 and glucagon receptors were determined by exposing cells expressing human glucagon receptor (hGLUC R), and human GLP-1 receptor (hGLP-1 R) to the listed compounds at increasing concentrations and measuring the formed cAMP as described in Methods.

The results for Exendin-4 derivatives with activity at the human GLP-1 receptor (hGLP-1 R) and the human glucagon receptor (hGLUC R) are shown in Table 4.

TABLE 4

EC50 values of exendin-4 peptide analogues at GLP-1 and Glucagon receptors (indicated in pM)

| SEQ ID NO | EC50 hGLP-1 R [pM] | EC50 hGLUC R [pM] |
| --- | --- | --- |
| 1 | 0.4 | >10000000 |
| 2 | 56.6 | 1.0 |
| 3 | 44333.3 | 1.8 |
| 4 | 3300.0 | 0.7 |
| 5 | 2190.0 | 0.6 |
| 6 | 9300.0 | 0.5 |
| 7 | 4190.0 | 2.4 |
| 8 | 5800.0 | 2.2 |
| 9 | 12200.0 | 2.2 |
| 10 | 45000.0 | 6.0 |
| 11 | 11700.0 | 0.9 |
| 12 | 20000.0 | 1.0 |
| 13 | 32100.0 | 3.1 |
| 14 | 52900.0 | 1.2 |
| 15 | 34500.0 | 2.2 |
| 16 | 19700.0 | 0.9 |
| 17 | 6940.0 | 1.0 |
| 18 | 25800.0 | 3.1 |
| 19 | 6640.0 | 0.7 |
| 20 | 38900.0 | 3.8 |
| 21 | 49700.0 | 1.4 |
| 22 | 8570.0 | 1.0 |
| 23 | 50700.0 | 3.5 |
| 24 | 8310.0 | 0.7 |
| 25 | 23100.0 | 0.8 |

Example 6

Comparison Testing

A selection of exendin-4 derivatives comprising the artificial amino acid 4-thiazolylalanine in position 1 has been tested in comparison to corresponding compounds that have histidine in position 1. Histidine at position 1 is essential for the activation of the receptor in glucagon but also in many related peptides including GLP-1 and exendin-4. Therefore it is surprising that the artificial amino acid 4-thiazolylalanine leads to an even higher activation of the receptor compared to identical compounds that have the natural histidine at position 1. Furthermore, the activation of the GLP-1 receptor which counterregulates the glucagon effect is surprisingly reduced by the introduction of the artificial amino acid 4-thiazolylalanine. This leads to even more selective glucagon receptor agonists with a higher GCG/GLP-1 activity ratio. The reference pair compounds and the corresponding EC50 values at GLP-1 and Glucagon receptors (indicated in pM) are given in Table 5.

TABLE 5

Comparison of exendin-4 derivatives comprising the artificial amino acid 4-thiazolylalanine in position 1 vs. exendin-4 derivatives having the natural amino acid histidine in position 1. EC50 values at GLP-1 and Glucagon receptors are indicated in pM.

| SEQ ID NO | Amino acid in position 1 | EC50 hGLP-1R | EC50 hGlucagon-R | Ratio |
|---|---|---|---|---|
| 2 | His | 56.6 | 1.0 | 57:1 |
| 3 | Tza | 44333.3 | 1.8 | 24630:1 |
| 26 | His | 1240.0 | 9.4 | 132:1 |
| 4 | Tza | 3300.0 | 0.7 | 4714:1 |
| 27 | His | 80.8 | 1.3 | 62:1 |
| 5 | Tza | 2190.0 | 0.6 | 3650:1 |
| 28 | His | 52.4 | 1.0 | 52:1 |
| 6 | Tza | 9300.0 | 0.5 | 18600:1 |
| 29 | His | 145.0 | 0.9 | 161:1 |
| 7 | Tza | 4190.0 | 2.4 | 1746:1 |
| 30 | His | 1180.0 | 6.5 | 182:1 |
| 8 | Tza | 5800.0 | 2.2 | 2636:1 |
| 31 | His | 941.0 | 4.1 | 230:1 |
| 10 | Tza | 45000.0 | 6.0 | 7500:1 |
| 32 | His | 18700.0 | 12.0 | 1558:1 |
| 11 | Tza | 11700.0 | 0.9 | 13000:1 |
| 33 | His | 159.0 | 1.1 | 145:1 |
| 12 | Tza | 20000.0 | 1.0 | 20000:1 |
| 34 | His | 363.0 | 1.4 | 259:1 |
| 15 | Tza | 34500.0 | 2.2 | 15682:1 |
| 35 | His | 934.0 | 7.1 | 132:1 |
| 15 | Tza | 19700.0 | 0.9 | 21888:1 |
| 36 | His | 358.5 | 1.4 | 256:1 |

Example 7

Effect of SEQ. ID 5 and SEQ. ID 6 on Glucose Release in Anesthetized Rats after S.C. Injection During the 2 hr pre-treatment period blood glucose stabilized at a level of about 6 mmol/l, representing normal fed values in rats. GCG at the dose of 30 µg/kg caused a rapid rise of blood glucose, which peaked after 30 minutes at blood glucose levels of about 10 to 11 mmol/l. The test compound SEQ. ID 5 at doses of 10, 20 and 30 µg/kg subcutaneously caused a dose-dependent increase of blood glucose, which peaked 30, 45 and 90 min after injection, respectively. The dose of 20 µg/kg of SEQ. ID 5 demonstrated a nearly comparable shape of blood glucose excursion compared to 30 µg/kg GCG (FIG. 1).

Figure 2:
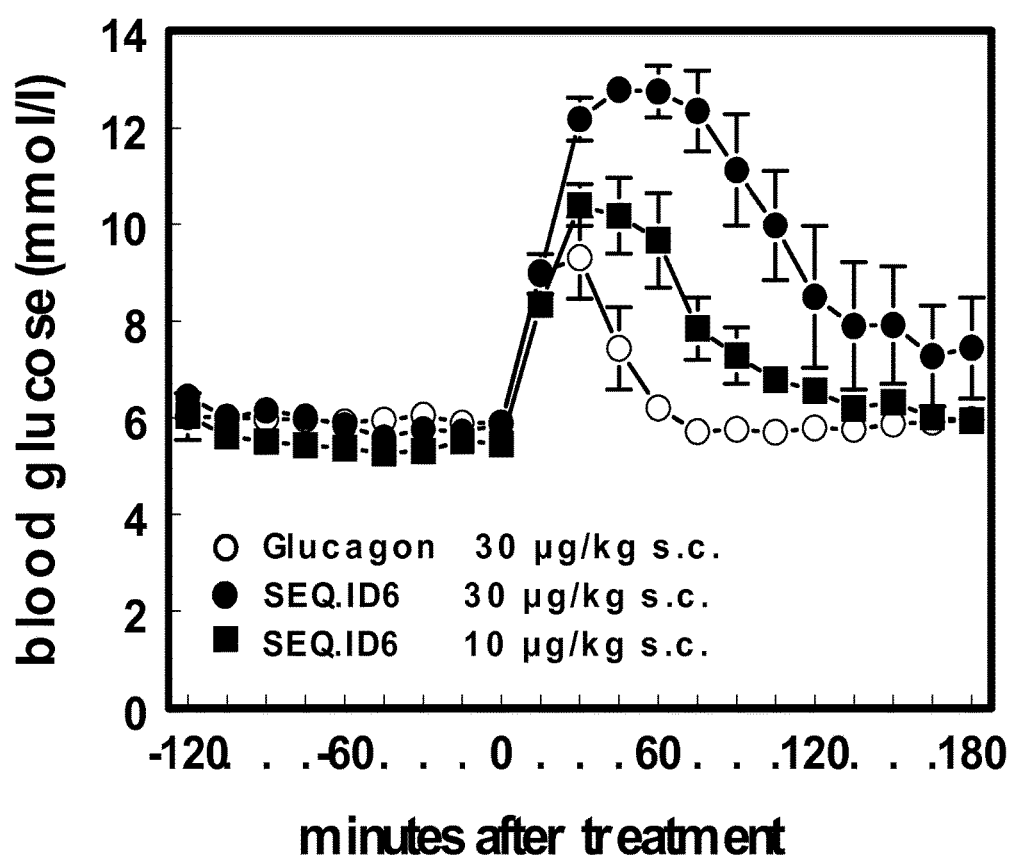

The test compound SEQ. ID 6 at doses of 10 and 30 µg/kg caused a dose-dependent increase of blood glucose, which peaked 30 and 60 min after injection, respectively. The dose of 10 µg/kg of SEQ. ID 6 demonstrated a more powerful blood glucose excursion compared to 30 µg/kg GCG (FIG. 2).

Example 8

Figure 3:
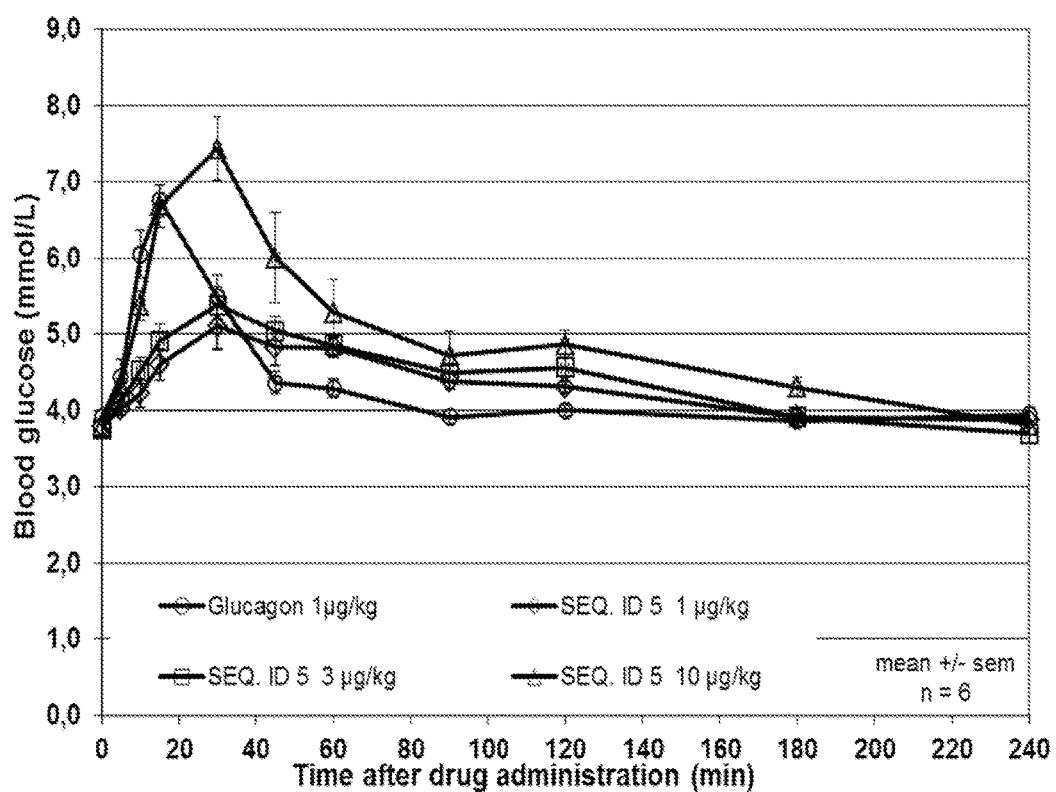
Figure 4:
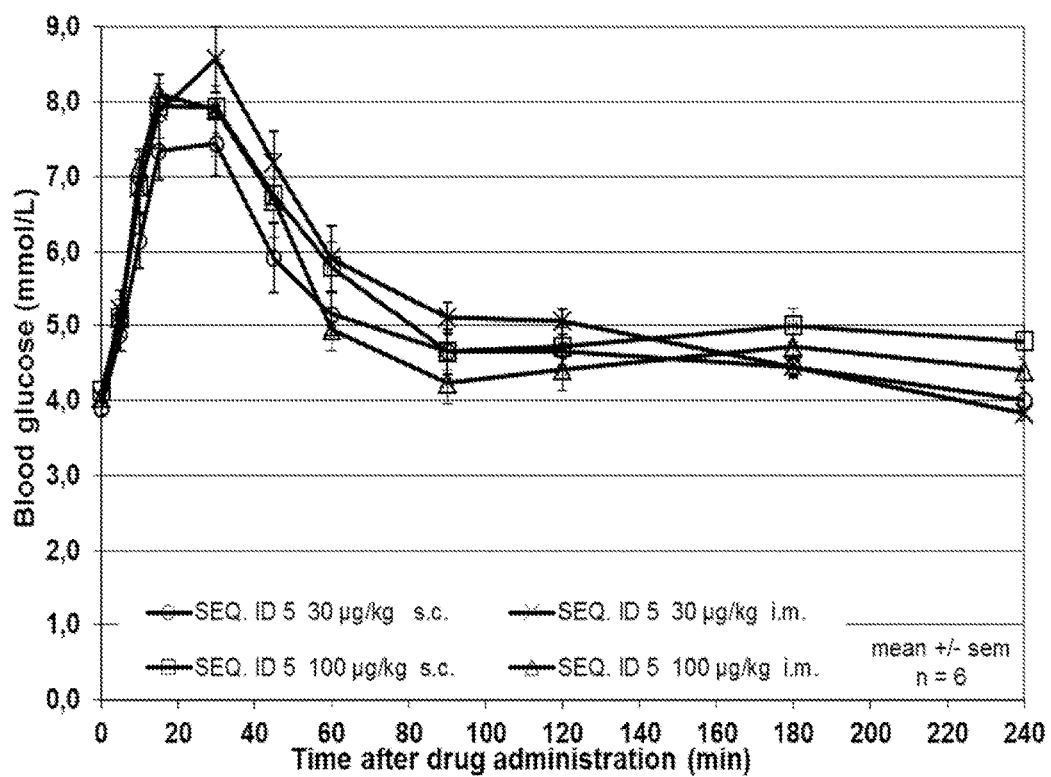

Effect of SEQ. ID. 5 and SEQ. ID 6 on Glucose Release in Normoglycemic Beagle Dogs after S.C. Injection In animals and humans injection of glucagon leads to a rapid recruitment of hepatic glycogen which is immediately broken down to glucose. This results in an acute but short lasting increase in blood glucose. In normoglycemic Beagle dogs subcutaneous (s.c.) injection of 1 µg/kg human glucagon leads to rapid increase of blood glucose by 2-3 mmol/L within 15 min. s.c. injection of SEQ. ID 5 and SEQ. ID 6 mimicked the effect of human glucagon on blood glucose. In the dog the net total glucose response (change in blood glucose AUC(0-240 min) from baseline) after injection of 1 µg/kg s.c. SEQ. ID 5 was similar to that of 1 µg/kg s.c. human glucagon. Blood glucose response to SEQ. ID 5 increased depending on the dose until a peak increase of ~3.5-4 mmol/L was reached with 10 µg/kg s.c. (FIG. 3). Beyond this higher doses of s.c. SEQ. ID 5 did no longer result in higher glucose excursion. In dog the onset of glucose response s.c. SEQ. ID 5 was similar to that of human glucagon while the duration of the glucose response was slightly longer. SEQ. ID 5 was active through all parenteral routes as subcutaneous, intramuscular and intravenous injections resulted in rapid and transient blood glucose increase. There was no difference in activity and blood glucose time-action profile between subcutaneously and intramuscularly injections SEQ. ID 5 in dogs (FIG. 4).

Figure 5:
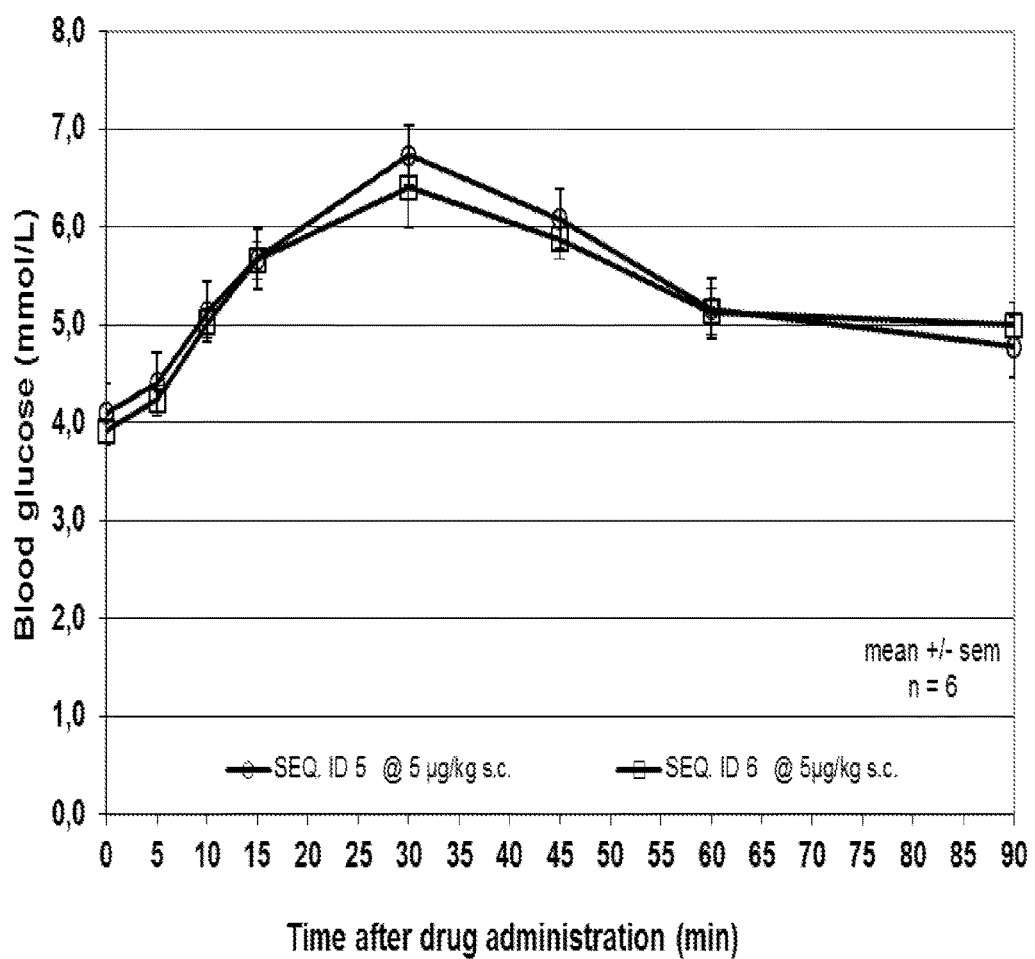

With respect to induction of a blood glucose response SEQ. ID 5 and SEQ. ID 6 were similarly active in normoglycemic dogs (FIG. 5).

TABLE 10

| SEQ. ID | Sequences sequence |
|---|---|
| 1 | H-G-E-G-T-F-T-S-D-L-S-K-Q-M-E-E-E-A-V-R-L-F-I-E-W-L-K-N-G-G-P-S-S-G-A-P-P-P-S-NH2 |
| 2 | H-S-Q-G-T-F-T-S-D-Y-S-K-Y-L-D-S-R-R-A-Q-D-F-V-Q-W-L-M-N-T-OH |
| 3 | Tza-S-Q-G-T-F-T-S-D-L-S-K-Q-Nle-E-S-R-R-A-Q-D-F-I-E-W-L-L-A-T-G-P-E-S-G-A-P-P-P-S-OH |
| 4 | Tza-S-Q-G-T-F-T-S-D-L-S-K-Q-L-E-S-R-R-A-Q-E-F-I-E-W-L-L-A-G-G-P-E-S-G-A-P-P-P-S-OH |
| 5 | Tza-S-Q-G-T-F-T-S-D-Y-S-K-Q-L-E-S-R-R-A-Q-E-F-I-E-W-L-L-A-G-G-P-E-S-G-A-P-P-P-S-OH |
| 6 | Tza-S-Q-G-T-F-T-S-D-Y-S-K-Q-L-E-S-R-R-A-Q-E-F-I-E-W-L-L-A-T-G-P-E-S-G-A-P-P-P-S-OH |
| 7 | Tza-S-Q-G-T-F-T-S-D-V-S-K-Q-L-E-S-R-R-A-Q-E-F-I-E-W-L-L-A-T-G-P-E-S-G-A-P-P-P-S-OH |
| 8 | Tza-S-Q-G-T-F-T-S-D-I-S-K-Q-L-E-S-R-R-A-Q-E-F-I-E-W-L-L-A-T-G-P-E-S-G-A-P-P-P-S-OH |

TABLE 10-continued

Sequences

| SEQ. ID | sequence |
|---|---|
| 9 | Tza-S-Q-G-T-F-T-S-D-V-S-K-Q-L-E-S-R-R-A-Q-E-F-I-E-W-L-L-A-G-G-P-E-S-G-A-P-P-P-S-OH |
| 10 | Tza-S-Q-G-T-F-T-S-D-Phg-S-K-Q-L-E-S-R-R-A-Q-E-F-I-E-W-L-L-A-T-G-P-E-S-G-A-P-P-P-S-OH |
| 11 | Tza-S-Q-G-T-F-T-S-D-1Nal-S-K-Q-L-E-S-R-R-A-Q-E-F-I-E-W-L-L-A-T-G-P-E-S-G-A-P-P-P-S-OH |
| 12 | Tza-S-Q-G-T-F-T-S-D-L-S-K-Q-L-E-S-R-R-A-Q-E-F-I-E-W-L-L-A-T-G-P-E-S-G-A-P-P-P-S-OH |
| 13 | Tza-S-Q-G-T-F-T-S-D-F-S-K-Q-Nle-E-S-R-R-A-Q-D-F-I-E-W-L-L-A-T-G-P-E-S-G-A-P-P-P-S-OH |
| 14 | Tza-S-Q-G-T-F-T-S-D-I-S-K-Q-Nle-E-S-R-R-A-Q-E-F-1-E-W-L-L-A-T-G-P-E-S-G-A-P-P-P-S-OH |
| 15 | Tza-S-Q-G-T-F-T-S-D-L-S-K-Q-L-E-S-R-R-A-Q-D-F-I-E-W-L-L-A-T-G-P-E-S-G-A-P-P-P-S-OH |
| 16 | Tza-S-Q-G-T-F-T-S-D-L-S-K-Q-Nle-E-S-R-R-A-Q-E-F-I-E-W-L-L-A-T-G-P-E-S-G-A-P-P-P-S-OH |
| 17 | Tza-S-Q-G-T-F-T-S-D-Y-S-K-Q-Nle-E-S-R-R-A-Q-E-F-I-E-W-L-L-A-T-G-P-E-S-G-A-P-P-P-S-OH |
| 18 | Tza-S-Q-G-T-F-T-S-D-2FPhe-S-K-Q-Nle-E-S-R-R-A-Q-D-F-I-E-W-L-L-A-T-G-P-E-S-G-A-P-P-P-S-OH |
| 19 | Tza-S-Q-G-T-F-T-S-D-1Nal-S-K-Q-Nle-E-S-R-R-A-Q-D-F-I-E-W-L-L-A-T-G-P-E-S-G-A-P-P-P-S-OH |
| 20 | Tza-S-Q-G-T-F-T-S-D-Chg-S-K-Q-Nle-E-S-R-R-A-Q-D-F-I-E-W-L-L-A-T-G-P-E-S-G-A-P-P-P-S-OH |
| 21 | Tza-S-Q-G-T-F-T-S-D-2FPhe-S-K-Q-L-E-S-R-R-A-Q-D-F-I-E-W-L-L-A-T-G-P-E-S-G-A-P-P-P-S-OH |
| 22 | Tza-S-Q-G-T-F-T-S-D-1Nal-S-K-Q-L-E-S-R-R-A-Q-D-F-I-E-W-L-L-A-T-G-P-E-S-G-A-P-P-P-S-OH |
| 23 | Tza-S-Q-G-T-F-T-S-D-Chg-S-K-Q-L-E-S-R-R-A-Q-D-F-I-E-W-L-L-A-T-G-P-E-S-G-A-P-P-P-S-OH |
| 24 | Tza-S-Q-G-T-F-T-S-D-Chg-S-K-Q-Nle-E-S-R-R-A-Q-E-F-I-E-W-L-L-A-T-G-P-E-S-G-A-P-P-P-S-OH |
| 25 | Tza-S-Q-G-T-F-T-S-D-Tle-S-K-Q-Nle-E-S-R-R-A-Q-E-F-I-E-W-L-L-A-T-G-P-E-S-G-A-P-P-P-S-OH |
| 26 | H-S-Q-G-T-F-T-S-D-L-S-K-Q-Nle-E-S-R-R-A-Q-D-F-I-E-W-L-L-A-T-G-P-E-S-G-A-P-P-P-S-OH |
| 27 | H-S-Q-G-T-F-T-S-D-L-S-K-Q-L-E-S-R-R-A-Q-E-F-I-E-W-L-L-A-G-G-P-E-S-G-A-P-P-P-S-OH |
| 28 | H-S-Q-G-T-F-T-S-D-Y-S-K-Q-L-E-S-R-R-A-Q-E-F-I-E-W-L-L-A-G-G-P-E-S-G-A-P-P-P-S-OH |
| 29 | H-S-Q-G-T-F-T-S-D-Y-S-K-Q-L-E-S-R-R-A-Q-E-F-I-E-W-L-L-A-T-G-P-E-S-G-A-P-P-P-S-OH |
| 30 | H-S-Q-G-T-F-T-S-D-V-S-K-Q-L-E-S-R-R-A-Q-E-F-I-E-W-L-L-A-T-G-P-E-S-G-A-P-P-P-S-OH |
| 31 | H-S-Q-G-T-F-T-S-D-I-S-K-Q-L-E-S-R-R-A-Q-E-F-I-E-W-L-L-A-T-G-P-E-S-G-A-P-P-P-S-OH |
| 32 | H-S-Q-G-T-F-T-S-D-Phg-S-K-Q-L-E-S-R-R-A-Q-E-F-I-E-W-L-L-A-T-G-P-E-S-G-A-P-P-P-S-OH |
| 33 | H-S-Q-G-T-F-T-S-D-1Nal-S-K-Q-L-E-S-R-R-A-Q-E-F-I-E-W-L-L-A-T-G-P-E-S-G-A-P-P-P-S-OH |
| 34 | H-S-Q-G-T-F-T-S-D-L-S-K-Q-L-E-S-R-R-A-Q-E-F-I-E-W-L-L-A-T-G-P-E-S-G-A-P-P-P-S-OH |
| 35 | H-S-Q-G-T-F-T-S-D-L-S-K-Q-L-E-S-R-R-A-Q-D-F-I-E-W-L-L-A-T-G-P-E-S-G-A-P-P-P-S-OH |
| 36 | H-S-Q-G-T-F-T-S-D-L-S-K-Q-Nle-E-S-R-R-A-Q-E-F-I-E-W-L-L-A-T-G-P-E-S-G-A-P-P-P-S-OH |

The invention claimed is:

1. A peptidic compound having the formula (I):

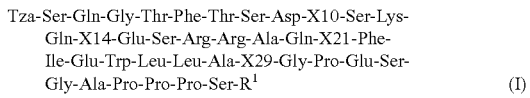

Tza-Ser-Gln-Gly-Thr-Phe-Thr-Ser-Asp-X10-Ser-Lys-
Gln-X14-Glu-Ser-Arg-Arg-Ala-Gln-X21-Phe-
Ile-Glu-Trp-Leu-Leu-Ala-X29-Gly-Pro-Glu-Ser-
Gly-Ala-Pro-Pro-Pro-Ser-R¹   (I)

wherein,
X10 represents an amino acid residue selected from Tyr, Leu, Val, Ile, Phe, Phenylglycine, 1-Naphthylalanine, 2-Fluorophenylalanine, Cyclohexylglycine and tert-Leucine;
X14 represents an amino acid residue selected from Leu and Nle;
X21 represents an amino acid residue selected from Asp and Glu;
X29 represents an amino acid residue selected from Gly and Thr; and
R¹ represents OH or NH₂;
or a salt or solvate thereof.

2. The peptidic compound of claim 1, wherein R¹ represents OH.

3. The peptidic compound of claim 1, wherein,
X10 represents Leu;
X14 represents an amino acid residue selected from Leu and Nle;
X21 represents an amino acid residue selected from Asp and Glu;
X29 represents an amino acid residue selected from Gly and Thr; and
R¹ represents OH;
or a salt or solvate thereof.

4. The peptidic compound of claim 1, wherein,
X10 represents Tyr;
X14 represents an amino acid residue selected from Leu and Nle;
X21 represents Glu;
X29 represents an amino acid residue selected from Gly and Thr; and
R¹ represents OH;
or a salt or solvate thereof.

5. The peptidic compound of claim 1, wherein,
X10 represents 1-Naphthylalanine;
X14 represents an amino acid residue selected from Leu and Nle;
X21 represents an amino acid residue selected from Asp and Glu;
X29 represents Thr; and
R¹ represents OH;
or a salt or solvate thereof.

6. The peptidic compound of claim 1, wherein,
X10 represents Cyclohexylglycine;
X14 represents an amino acid residue selected from Leu and Nle;
X21 represents an amino acid residue selected from Asp and Glu;
X29 represents Thr; and
R¹ represents OH;
or a salt or solvate thereof.

7. The peptidic compound of claim 1, wherein,
X10 represents an amino acid residue selected from Tyr, Leu, Val, Ile, Phenylglycine, 1-Naphthylalanine, 2-Fluorophenylalanine and Cyclohexylglycine;
X14 represents Leu;
X21 represents an amino acid residue selected from Asp and Glu;
X29 represents an amino acid residue selected from Gly and Thr; and
R¹ represents OH;
or a salt or solvate thereof.

8. The peptidic compound of claim 1, wherein,
X10 represents an amino acid residue selected from Tyr, Leu, Ile, Phe, 1-Naphthylalanine, Cyclohexylglycine and tert-Leucine;
X14 represents Nle;
X21 represents an amino acid residue selected from Asp and Glu;
X29 represents Thr; and
R¹ represents OH;
or a salt or solvate thereof.

9. The peptidic compound of claim 1, wherein,
X10 represents an amino acid residue selected from Leu, Phe, 1-Naphthylalanine, 2-Fluorophenylalanine and Cyclohexylglycine;
X14 represents an amino acid residue selected from Leu and Nle;
X21 represents Asp;
X29 represents Thr; and
R¹ represents OH;
or a salt or solvate thereof.

10. The peptidic compound of claim 1, wherein,
X10 represents an amino acid residue selected from Tyr, Leu, Val, Ile, Phenylglycine, 1-Naphthylalanine, Cyclohexylglycine and tert-Leucine;
X14 represents an amino acid residue selected from Leu and Nle;
X21 represents Glu;
X29 represents an amino acid residue selected from Gly and Thr; and
R¹ represents OH;
or a salt or solvate thereof.

11. The peptidic compound of claim 1, wherein,
X10 represents an amino acid residue selected from Tyr, Leu, Val, Ile, Phe, Phenylglycine, 1-Naphthylalanine, 2-Fluorophenylalanine, Cyclohexylglycine and tert-Leucine;
X14 represents an amino acid residue selected from Leu and Nle;
X21 represents an amino acid residue selected from Asp and Glu;
X29 represents Thr; and
R¹ represents OH;
or a salt or solvate thereof.

12. The peptidic compound of claim 1, wherein,
X10 represents an amino acid residue selected from Tyr, Leu and Val;
X14 represents Leu;
X21 represents Glu;
X29 represents Gly; and
R¹ represents OH;
or a salt or solvate thereof.

13. The peptidic compound of claim 1, wherein the peptidic compound is selected from the compounds of SEQ ID NO: 3-25 or a salt or solvate thereof.

14. The peptidic compound of claim 1, wherein the peptidic compound is selected from the compounds of SEQ ID NO:3, 5, 6, 9, 15, 20, 23, 24 and 25 or a salt or solvate thereof.

15. A pharmaceutical composition comprising the peptidic compound of claim 1 and at least one pharmaceutically acceptable carrier.

16. A method for treating hypoglycemia or type 2 diabetes mellitus in a patient in need thereof, the method comprising administering to the patient a therapeutically effective amount of at least one peptidic compound of claim 1.

17. A pharmaceutical composition comprising at least one peptidic compound of claim 1 or a physiologically acceptable salt or solvent thereof.

18. A method for treating hypoglycemia in a patient in need thereof, the method comprising administering to the patient a therapeutically effective amount of at least one peptidic compound of claim 1.

19. The method of claim 18, wherein the at least one peptidic compound and the at least one other compound are administered simultaneously, separately, or sequentially.

20. The method of claim 18, wherein the at least one peptidic compound is administered parenterally.

21. A method for treating hypoglycemia in a patient in need thereof, the method comprising administering to the patient a therapeutically effective amount of at least one peptidic compound of claim 1 and a therapeutically effective amount of at least one other compound useful for treating hypoglycemia.

* * * * *

UNITED STATES PATENT AND TRADEMARK OFFICE
CERTIFICATE OF CORRECTION

Page 1 of 1

PATENT NO. : 9,932,381 B2
APPLICATION NO. : 14/738261
DATED : April 3, 2018
INVENTOR(S) : Haack et al.

It is certified that error appears in the above-identified patent and that said Letters Patent is hereby corrected as shown below:

In the Claims

In Claim 19, Column 49, Line 10, the text reading "The method of claim 18" should read -- The method of claim 21 --.

Signed and Sealed this
Twenty-third Day of April, 2019

Andrei Iancu
*Director of the United States Patent and Trademark Office*